US012608083B2

(12) United States Patent
Lee et al.

(10) Patent No.: US 12,608,083 B2
(45) Date of Patent: Apr. 21, 2026

(54) WEARABLE DEVICE FOR PROVIDING HAPTIC FEEDBACK AND OPERATION METHOD THEREOF

(71) Applicant: Samsung Electronics Co., Ltd., Suwon-si (KR)

(72) Inventors: Dongseop Lee, Suwon-si (KR); Hakjung Kim, Suwon-si (KR); Hyoungsu Kim, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 407 days.

(21) Appl. No.: 17/720,567

(22) Filed: Apr. 14, 2022

(65) Prior Publication Data

US 2022/0374080 A1     Nov. 24, 2022

Related U.S. Application Data

(63) Continuation of application No. PCT/KR2022/004216, filed on Mar. 25, 2022.

(30) Foreign Application Priority Data

May 6, 2021     (KR) ........................ 10-2021-0058853
Jul. 1, 2021     (KR) ........................ 10-2021-0086719

(51) Int. Cl.
*G06F 3/01* (2006.01)
*A61B 5/00* (2006.01)
(Continued)

(52) U.S. Cl.
CPC ............ *G06F 3/016* (2013.01); *A61B 5/1118* (2013.01); *A61B 5/441* (2013.01); *A61B 5/6802* (2013.01); *G16H 40/63* (2018.01)

(58) Field of Classification Search
CPC ... A61B 5/0533; A61B 5/1118; A61B 5/1123; A61B 5/441; A61B 5/6802;
(Continued)

(56) References Cited

U.S. PATENT DOCUMENTS 9,781,984 B2     10/2017 Baranski et al.
10,285,645 B2     5/2019 Bushnell et al.
(Continued)

FOREIGN PATENT DOCUMENTS

EP          2778850 A1     9/2014
EP          3416028 A1     12/2018
(Continued)

OTHER PUBLICATIONS

Extended European Search Report dated May 27, 2024, issued in European Patent Application 22798998.5.
(Continued)

*Primary Examiner* — Alex M Valvis
*Assistant Examiner* — Anna Roberts
(74) *Attorney, Agent, or Firm* — Jefferson IP Law, LLP

(57) ABSTRACT

A method, performed by a wearable device, of providing haptic feedback to a user is provided. The method includes obtaining profile data of the user, obtaining biometric data of the user by using one or more biosensors, calculating, based on the profile data and the biometric data of the user, a target contact pressure to be applied to a body of the user by one or more haptic actuators, measuring a current contact pressure applied to the body of the user by the one or more haptic actuators by using one or more pressure sensors, and adjusting the current contact pressure of the one or more haptic actuators based on the current contact pressure and the target contact pressure.

20 Claims, 24 Drawing Sheets

(51) Int. Cl.
  *A61B 5/11* (2006.01)
  *G16H 40/63* (2018.01)

(58) Field of Classification Search
  CPC ... A61B 5/6804; A61B 5/7264; A61B 5/7455;
    A61B 2562/0219; G06F 1/163; G06F
    3/011; G06F 3/016; G16H 20/30; G16H
    40/63; G16H 50/20; G16H 50/30
  See application file for complete search history.

(56) References Cited

U.S. PATENT DOCUMENTS

| | | | |
|---|---|---|---|
| 10,517,535 | B2 | 12/2019 | Min et al. |
| 10,559,174 | B2 | 2/2020 | Nagisetty et al. |
| 11,042,130 | B2 | 6/2021 | Aghara et al. |
| 11,324,450 | B2 | 5/2022 | Joe et al. |
| 2014/0267076 | A1 * | 9/2014 | Birnbaum ............... G06F 3/016 |
| | | | 340/407.1 |
| 2016/0210826 | A1 | 7/2016 | Kosonen et al. |
| 2016/0378186 | A1 | 12/2016 | Kim |
| 2018/0356888 | A1 * | 12/2018 | Rihn ....................... G01L 5/103 |
| 2018/0356890 | A1 * | 12/2018 | Zhang ..................... G06F 3/014 |
| 2019/0138705 | A1 | 5/2019 | Kim et al. |
| 2020/0089003 | A1 | 3/2020 | Lee et al. |
| 2021/0068277 | A1 | 3/2021 | Mulliken et al. |

FOREIGN PATENT DOCUMENTS

| | | |
|---|---|---|
| KR | 10-2014-0113408 A | 9/2014 |
| KR | 10-2015-0099019 A | 8/2015 |
| KR | 10-2018-0011458 A | 2/2018 |
| KR | 10-2018-0135804 A | 12/2018 |
| KR | 10-2020-0055933 A | 5/2020 |

OTHER PUBLICATIONS

International Search Report dated Jul. 1, 2022, issued in International Application No. PCT/KR2022/004216.
Kozlowska; "Studying tactile sensitivity—population approach"; Anthropological Review, vol. 61, pp. 3-30; Poznan 1998.
"Human Sensitivity Responses to Vibrotactile Stimulation on the Hand: Measurement of Absolute Thresholds"; Journal of the Ergonomics Society of Korea, vol. 17, No. 2, 1998.
Lundstrom et al. "Vibrotactile and thermal perception and its relation to finger skin thickness"; Clinical Neurophysiology Practice 3 (2018) 33-39.
Kasozi et al."A study on visual, audio and tactile reaction time among medical students at Kampala International University in Uganda"; African Health Science; Makerere Medical School; Afr Health Sci. Sep. 2018; 18(3): 828-836; doi: 10.4314/ahs.v18i3.42; https://www.ncbi.nlm.nih.gov/pmc/articles/PMC6307023/.
Ng et al. "Finger Response Times to Visual, Auditory and Tactile Modality Stimuli"; Proceedings of the International MultiConference of Engineers and Computer Scientists 2012 vol. II; IMECS 2012, Mar. 14-16, 2012; Hong Kong.
Prezi; https://prezi.com/ksjdkagxtk6f/presentation/?frame=8de9a236718798ce1c61654ca0a683ce35c9c79a.
European Notice of Allowance dated Nov. 4, 2024, issued in European Application No. 22798998.5.
European Notice of Allowance dated Mar. 10, 2026, issued in European Application No. 25159464.4.

* cited by examiner

FIG. 1

OBTAIN USER PROFILE DATA —— S310

OBTAIN BIOMETRIC DATA FROM BIOSENSOR —— S320

CALCULATE TARGET CONTACT PRESSURE BASED ON USER PROFILE DATA AND BIOMETRIC DATA —— S330

MEASURE CURRENT CONTACT PRESSURE WITH PRESSURE SENSOR —— S340

ADJUST CURRENT CONTACT PRESSURE OF HAPTIC ACTUATOR TO EQUAL TARGET CONTACT PRESSURE —— S350

PROVIDE HAPTIC FEEDBACK —— S360

FIG. 4

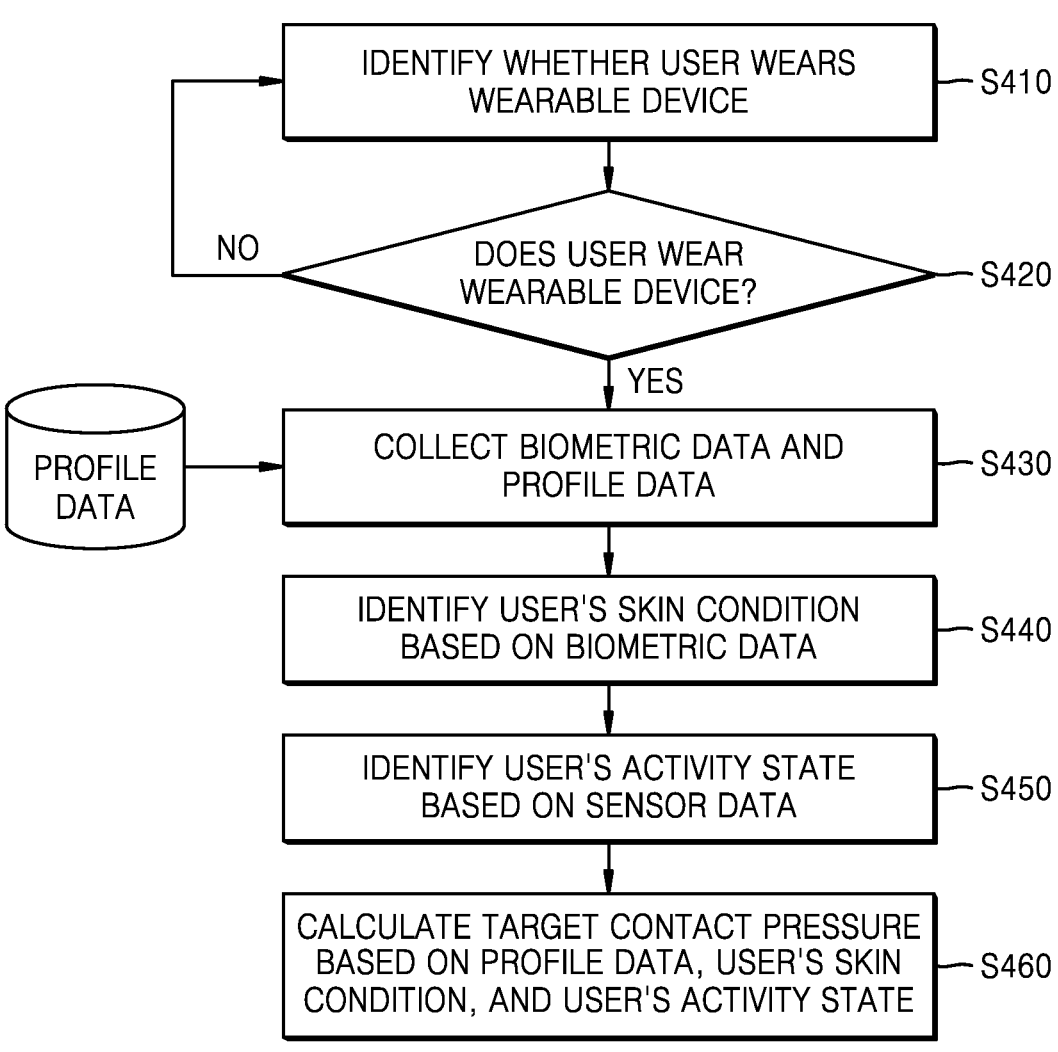

IDENTIFY WHETHER USER WEARS WEARABLE DEVICE — S410

DOES USER WEAR WEARABLE DEVICE? — S420

NO

YES

PROFILE DATA

COLLECT BIOMETRIC DATA AND PROFILE DATA — S430

IDENTIFY USER'S SKIN CONDITION BASED ON BIOMETRIC DATA — S440

IDENTIFY USER'S ACTIVITY STATE BASED ON SENSOR DATA — S450

CALCULATE TARGET CONTACT PRESSURE BASED ON PROFILE DATA, USER'S SKIN CONDITION, AND USER'S ACTIVITY STATE — S460

Actuator —1400

1410

——————— Up-move Gear (UG) —1412
- - - - - - - Down-move Gear (DG) —1414
- - - - - - Left-move Gear (LG) —1416
- - — - - Right-move Gear (RG) —1418

Actuator-A (A) Normal position (A) Adjustable position (A) Movement range

1401

1400

1403    1402

1404

Rotate UG & Rotate RG
→ Move to diagonal position

FIG. 14B
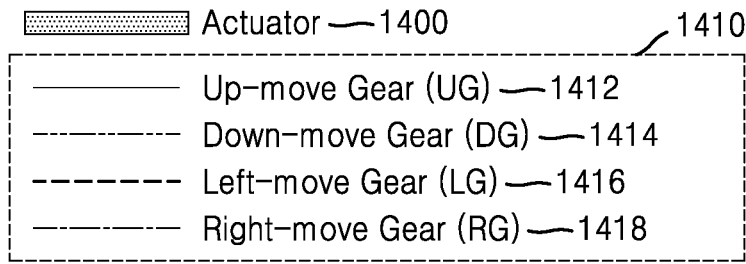
Actuator —1400
1410
Up-move Gear (UG) —1412
Down-move Gear (DG) —1414
Left-move Gear (LG) —1416
Right-move Gear (RG) —1418
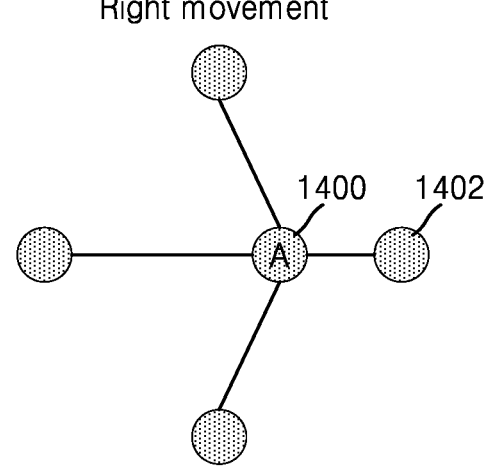
Actuator-A
Up movement
—1401
—1400
Actuator-A
Right movement
1400    1402
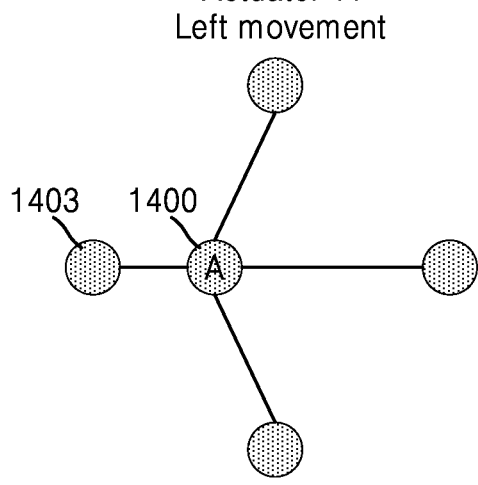
Actuator-A
Left movement
1403    1400
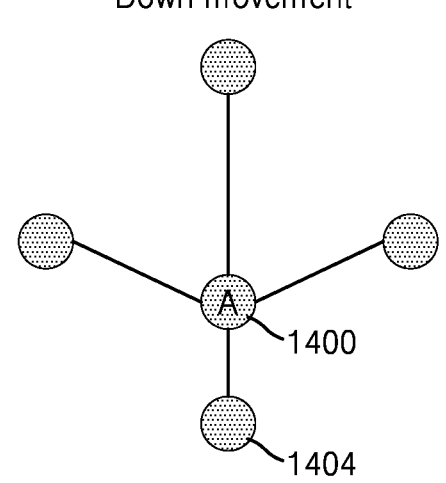
Actuator-A
Down movement
—1400
—1404

FIG. 17C

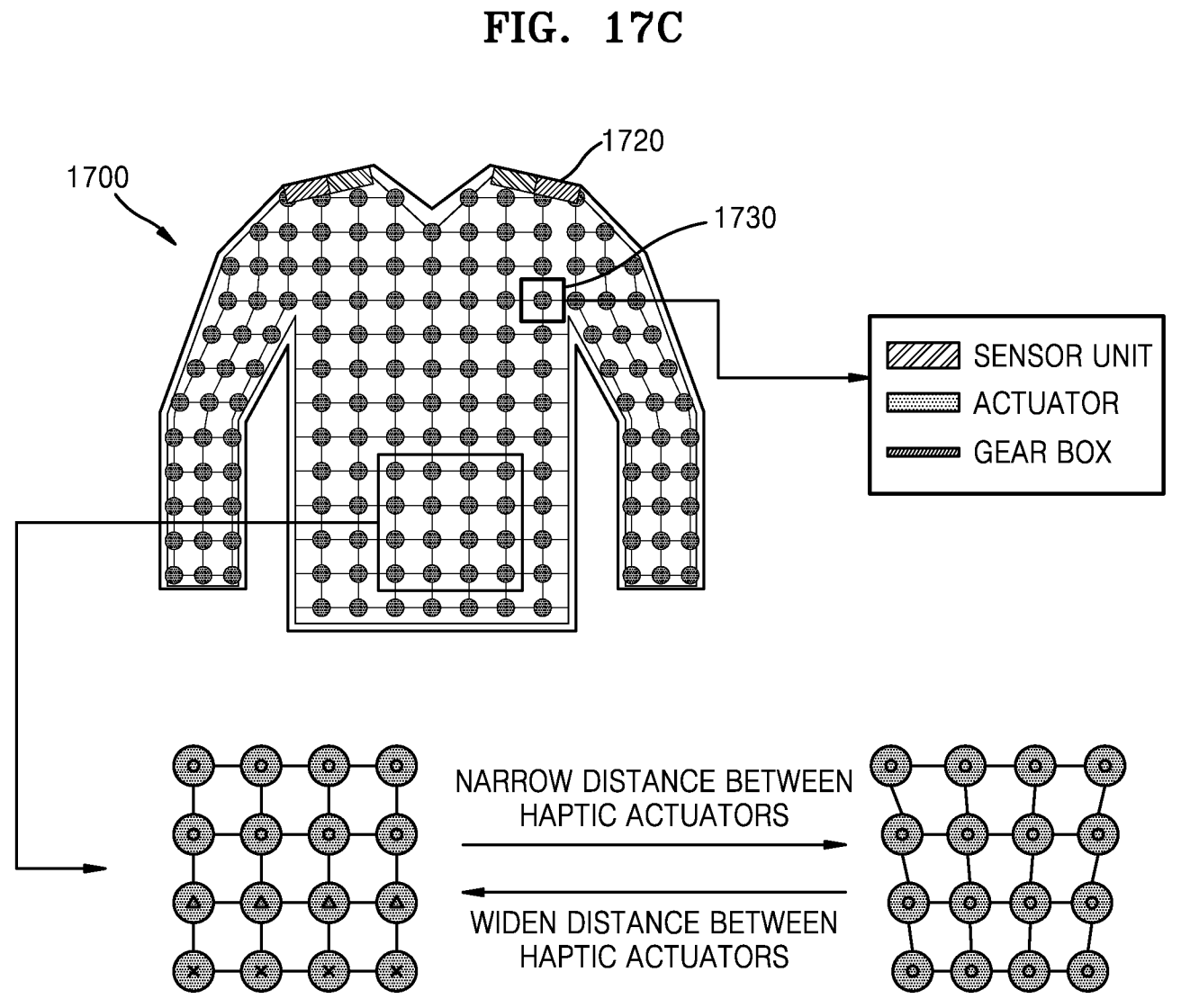

SENSOR UNIT

ACTUATOR

GEAR BOX

1730

1720

1700

NARROW DISTANCE BETWEEN HAPTIC ACTUATORS

WIDEN DISTANCE BETWEEN HAPTIC ACTUATORS

FIG. 19

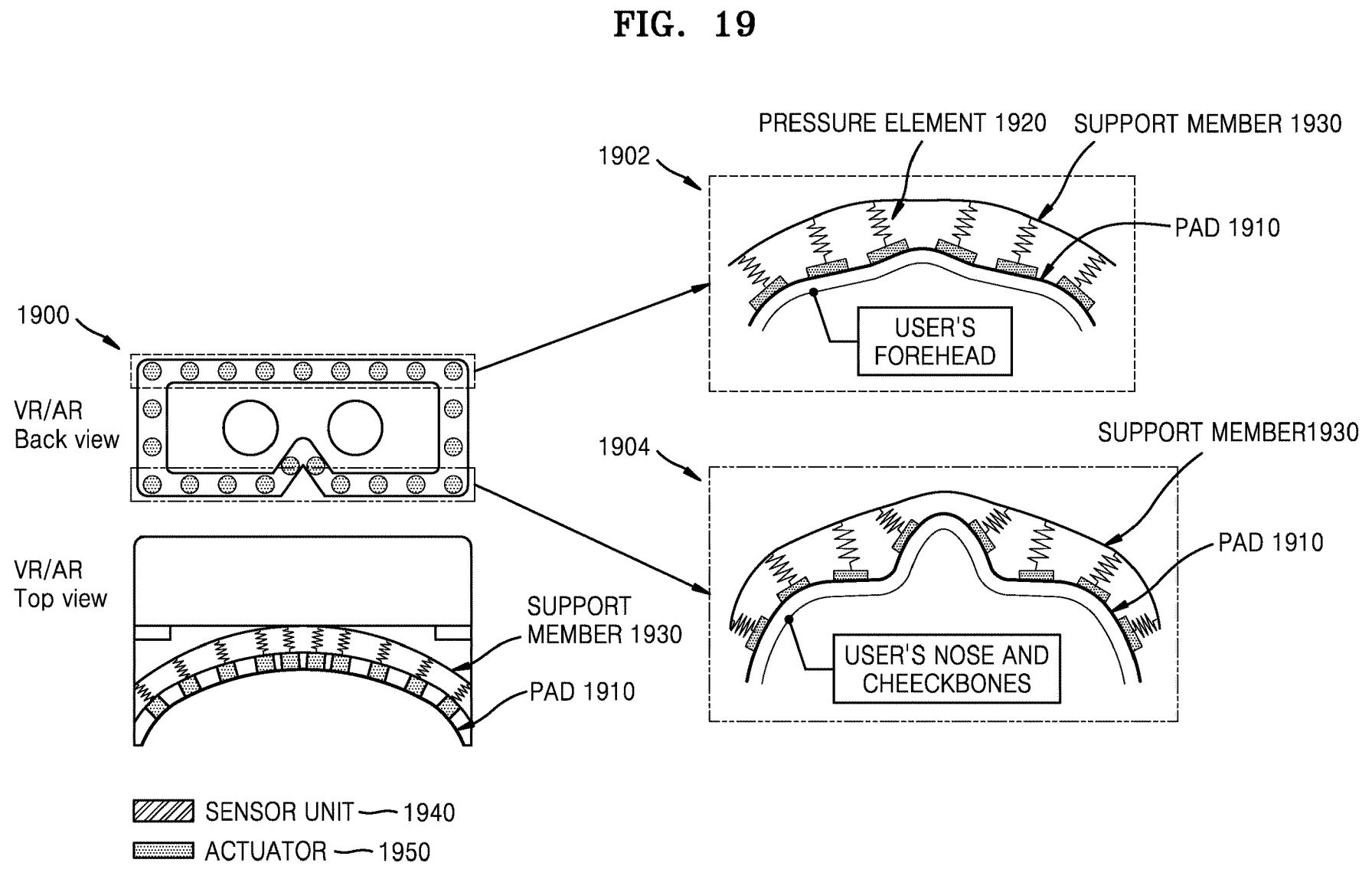

PRESSURE ELEMENT 1920    SUPPORT MEMBER 1930

PAD 1910

USER'S FOREHEAD

1902

SUPPORT MEMBER1930

PAD 1910

USER'S NOSE AND CHEECKBONES

1904

1900

VR/AR Back view

VR/AR Top view

SUPPORT MEMBER 1930

PAD 1910

SENSOR UNIT —1940

ACTUATOR —1950

WEARABLE DEVICE FOR PROVIDING HAPTIC FEEDBACK AND OPERATION METHOD THEREOF

CROSS-REFERENCE TO RELATED APPLICATION(S)

This application is a continuation application, claiming priority under § 365(c), of an International application No. PCT/KR2022/004216, filed on Mar. 25, 2022, which is based on and claims the benefit of a Korean patent application number 10-2021-0058853, filed on May 6, 2021, in the Korean Intellectual Property Office, and of a Korean patent application number 10-2021-0086719, filed on Jul. 1, 2021, in the Korean Intellectual Property Office, the disclosure of each of which is incorporated by reference herein in its entirety.

TECHNICAL FIELD

The disclosure relates to a haptic feedback providing device and operation method thereof.

BACKGROUND ART

Various types of wearable devices such as smart watches, smart bands, smart clothes, and head-mounted displays are being provided to users. Wearable devices may provide improved device use experience to users by providing haptic feedback to the users while performing operations of the wearable devices.

When a wearable device provides haptic feedback to a user, a degree of a user's perception of the haptic feedback may vary according to each user of the wearable device. To provide an appropriate haptic feedback for each user with a different degree of perception of haptic feedback, it is necessary to determine an appropriate contact pressure at which a haptic actuator for generating the haptic feedback is in contact with a user's body.

Accordingly, a specific method for providing haptic feedback to a user is presented.

The above information is presented as background information only to assist with an understanding of the disclosure. No determination has been made, and no assertion is made, as to whether any of the above might be applicable as prior art with regard to the disclosure.

DESCRIPTION OF EMBODIMENTS

Technical Problem

Aspects of the disclosure are to address at least the above-mentioned problems and/or disadvantages and to provide at least the advantages described below. Accordingly, an aspect of the disclosure is to provide a wearable device for providing haptic feedback to a user and an operation method thereof.

Additional aspects will be set forth in part in the description which follows and, in part, will be apparent from the description, or may be learned by practice of the presented embodiments.

Technical Solution to Problem

In accordance with an aspect of the disclosure, a wearable device is provided. The wearable device for providing haptic feedback includes a sensor unit configured to obtain a plurality of types of sensor data, the sensor unit including one or more biosensors configured to obtain biometric data of a user and one or more pressure sensors configured to obtain data regarding a contact pressure applied to a body of the user by one or more haptic actuators, the one or more haptic actuators configured to provide haptic feedback to the user, a memory storing one or more instructions, and one or more processors configured to execute the one or more instructions stored in the memory to obtain profile data of the user, obtain the biometric data of the user from the one or more biosensors, calculate, based on the profile data and the biometric data of the user, a target contact pressure to be applied to the body of the user by the one or more haptic actuators, measure a current contact pressure applied to the body of the user by the one or more haptic actuators by using the one or more pressure sensors, and adjust the current contact pressure of the one or more haptic actuators based on the current contact pressure and the target contact pressure.

In accordance with an aspect of the disclosure, a method, performed by a wearable device is provided. The method of providing haptic feedback includes obtaining profile data of a user, obtaining biometric data of the user by using one or more biosensors, calculating, based on the profile data and the biometric data of the user, a target contact pressure to be applied to a body of the user by one or more haptic actuators, measuring a current contact pressure applied to the body of the user by the one or more haptic actuators by using one or more pressure sensors, and adjusting the current contact pressure of the one or more haptic actuators based on the current contact pressure and the target contact pressure.

Wherein the biometric data of the user includes sensor data for identifying at least one of a skin condition or an activity state of the user, and wherein the profile data of the user includes information about at least one of 'an age, a gender, body attributes, or a skin type of the user.

Wherein the calculating of the target contact pressure comprises determining the target contact pressure by applying the profile data of the user, the identified skin condition, and the identified activity state to an artificial intelligence model trained to determine the target contact pressure.

Wherein the one or more haptic actuators are a plurality of haptic actuators, the one or more pressure sensors are a plurality of pressure sensors, and the one or more biosensors are a plurality of biosensors, wherein the calculating of the target contact pressure comprises respectively calculating target contact pressures of the plurality of haptic actuators based on the profile data and the biometric data of the user, and wherein the measuring of the current contact pressure comprises respectively measuring current contact pressures of the plurality of haptic actuators by using the plurality of pressure sensors.

The method further comprises selecting, based on the current contact pressures of the plurality of haptic actuators, one or more haptic actuators that have a current contact pressure to be adjusted from among the plurality of haptic actuators, wherein the adjusting of the current contact pressure of the one or more haptic actuators comprises adjusting the current contact pressure of the selected one or more haptic actuators.

The method further comprises identifying, based on the biometric data, whether a skin condition of the user has changed, wherein the calculating of the target contact pressure comprises, when the skin condition of the user is identified as having changed, changing the target contact pressures of the plurality of haptic actuators based on the profile data and the biometric data of the user, and wherein the adjusting of the current contact pressure of the one or more haptic actuators comprises readjusting a current contact pressure of at least some of the plurality of haptic actuators.

The method further comprises obtaining a plurality of types of sensor data from a sensor unit; and identifying whether an activity state of the user has changed based on at least some of the plurality of types of sensor data obtained from the sensor unit, wherein the calculating of the target contact pressure comprises, when the activity state of the user is identified as having changed, changing the target contact pressure to a new target contact pressure based on a degree of change in the target contact pressure that occurred before the activity state of the user is changed.

Wherein the adjusting of the current contact pressure comprises readjusting a current contact pressure of at least some of the plurality of haptic actuators, based on the new target contact pressure and a current contact pressure sensed by each of the plurality of pressure sensors.

Wherein the current contact pressure is adjusted to position the wearable device closer to the user's body in response to the current contact pressure being less than the target contact pressure.

wherein the current contact pressure is adjusted to position the wearable device further from the user's body in response to the current contact pressure being greater than the target contact pressure.

Wherein the contact pressure is adjusted by one of tightening or loosening at least one strap.

Wherein the contact pressure is adjusted by one of flued injection or fluid extraction.

Wherein the adjusting of the current contact pressure comprises adjusting the current contact pressure of the selected one or more haptic actuators by adjusting a distance between the selected one or more haptic actuators and each of other haptic actuators adjacent thereto.

The method further comprises comparing the distance between the selected one or more haptic actuators and the adjacent haptic actuators with a threshold value, and adjusting the distance in response to the distance being less than a threshold value.

The method further comprises deactivating at least some of the adjacent haptic actuators with the distance therebetween less than the threshold value.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF DRAWINGS

The above and other aspects, features, and advantages of certain embodiments of the disclosure will be more apparent from the following description taken in conjunction with the accompanying drawings, in which:

FIG. 1 is a diagram for describing wearable devices that provide haptic feedback according to an embodiment of the disclosure;

FIG. 4 is a flowchart of a method, performed by a wearable device, of determining a target contact pressure, according to an embodiment of the disclosure;

FIG. 6 is a diagram for describing a method, performed by a wearable device, of identifying a change in a skin condition and obtaining a first target contact pressure, according to an embodiment of the disclosure;

FIG. 13 is a diagram for describing a method, performed by a wearable device, of adjusting a distance between a plurality of haptic actuators in order to adjust current contact pressures of the plurality of haptic actuators, according to an embodiment of the disclosure;

FIG. 14B is a diagram for further describing the structure of FIG. 14A according to an embodiment of the disclosure;

FIG. 17C is a diagram for describing a method of adjusting a current contact pressure of a haptic actuator by adjusting a distance between haptic actuators when a wearable device is smart clothing, according to an embodiment of the disclosure;

5

Figure 18A:
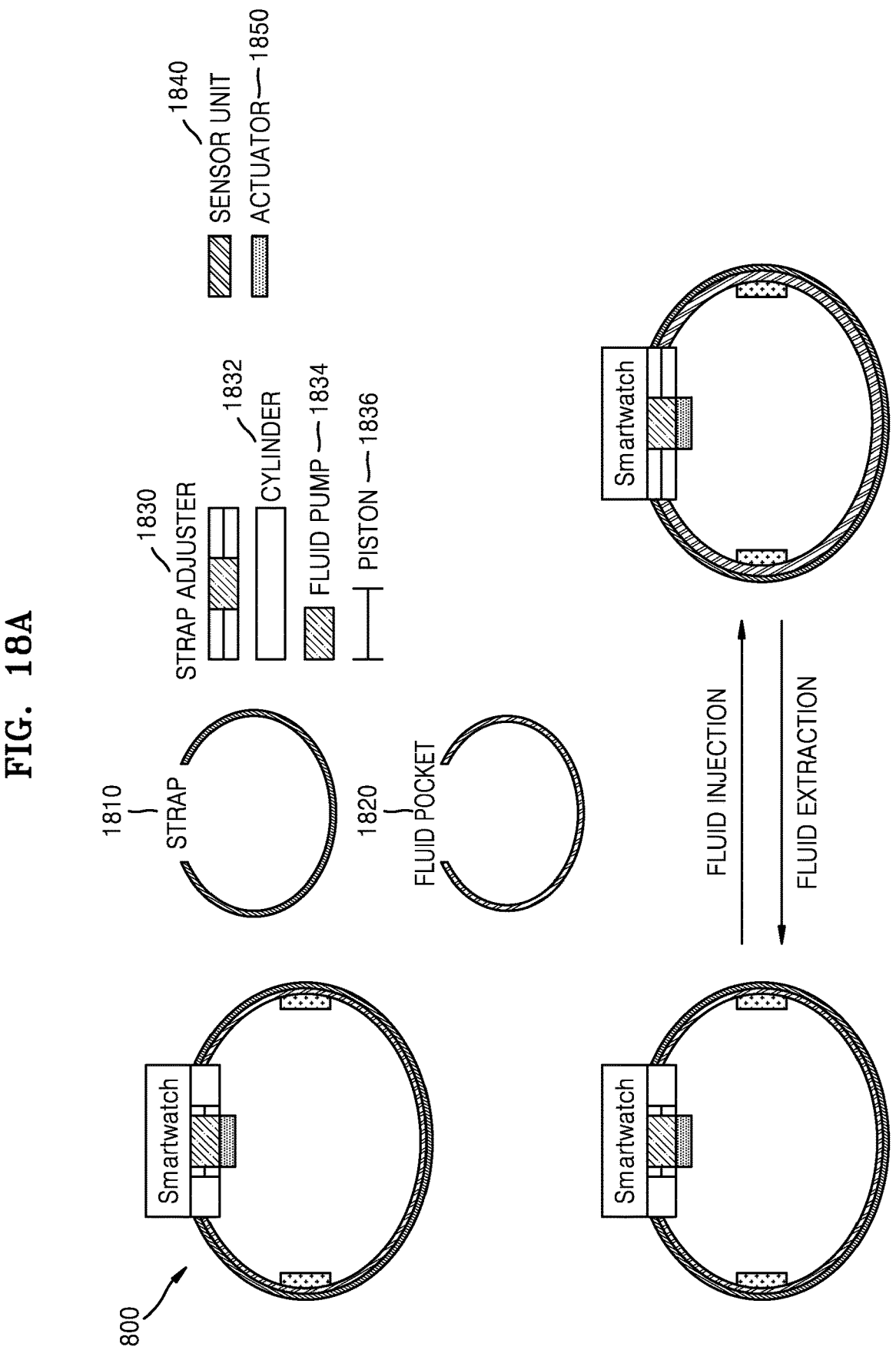
FIG. 18A is a diagram for describing a method of adjusting a current contact pressure of a haptic actuator by using a fluidic pressure when a wearable device is a smart watch, according to an embodiment of the disclosure.
Figure 18B:
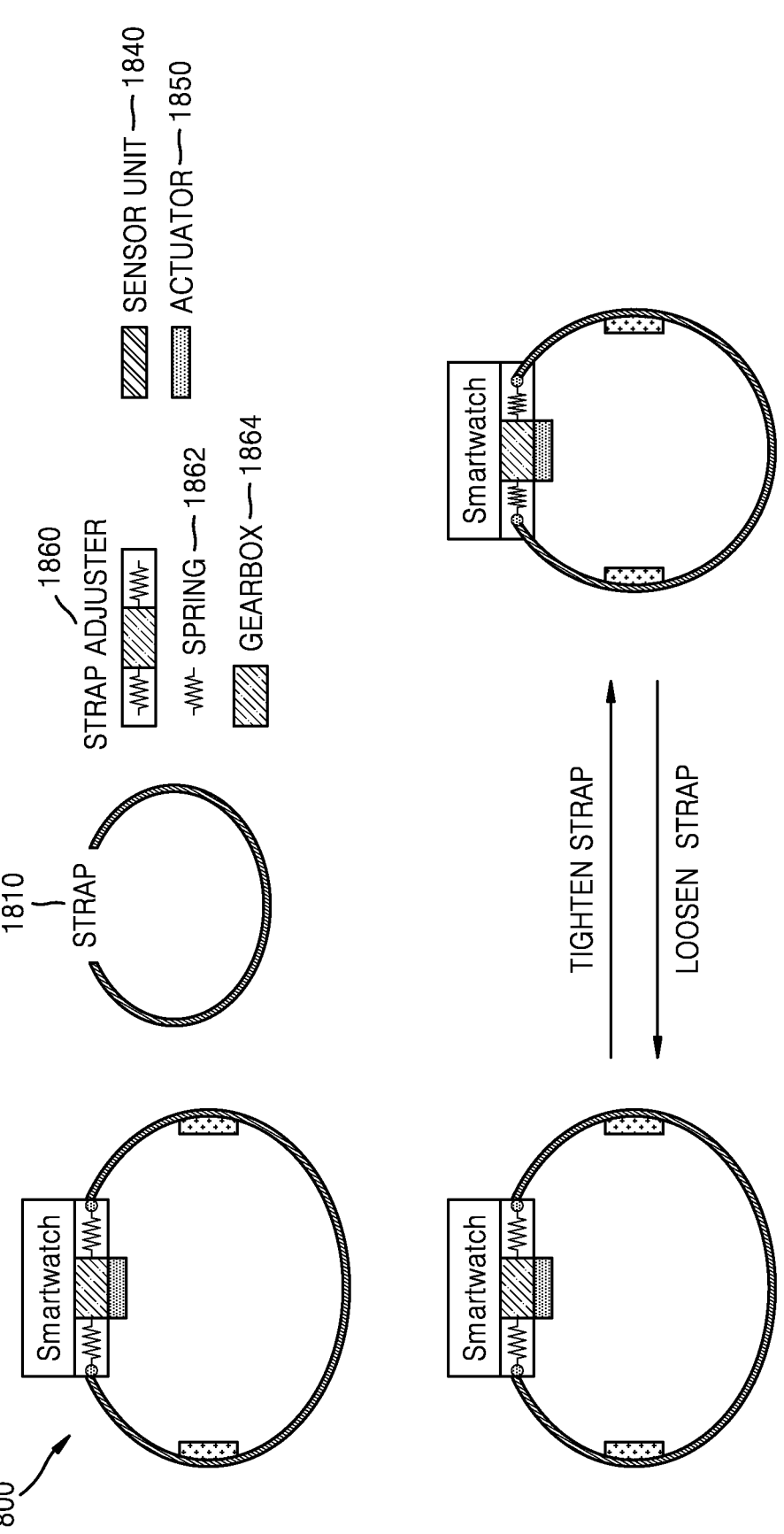
Figure 20:
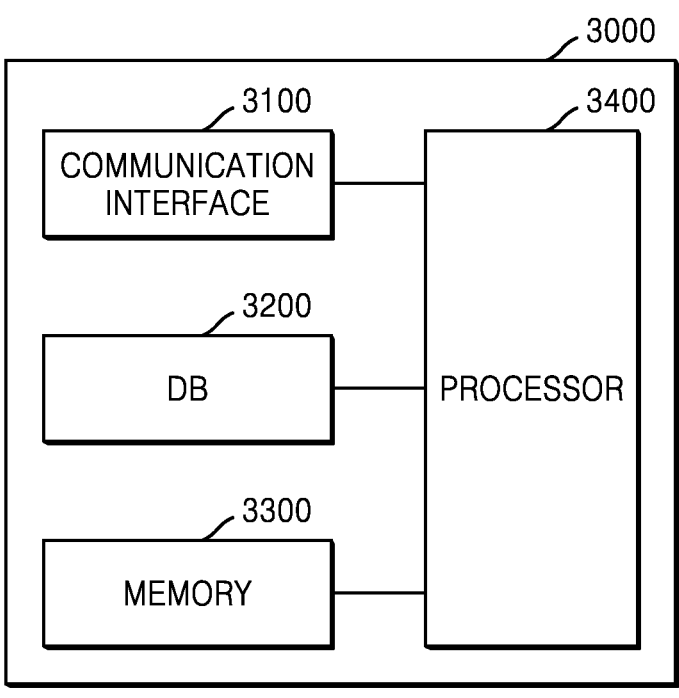

FIG. 18B is a diagram for describing another method of adjusting a current contact pressure of a haptic actuator by adjusting a length of a strap when a wearable device is a smart watch, according to an embodiment of the disclosure;

FIG. 19 is a diagram for describing a method of adjusting a current contact pressure of a haptic actuator by applying pressure to the haptic actuator when a wearable device is a head-mounted display, according to an embodiment of the disclosure; and FIG. 20 is a block diagram of a configuration of a server according to an embodiment of the disclosure.

MODE OF DISCLOSURE

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the applicant to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise.

Throughout the disclosure, the expression "at least one of a, b or c" indicates only a, only b, only c, both a and b, both a and c, both b and c, all of a, b, and c, or variations thereof.

Terms used in the specification will now be briefly described and then the disclosure will be described in detail.

The terms used in the disclosure are general terms currently widely used in the art based on functions described in the disclosure, but may have different meanings according to an intention of a technician engaged in the art, precedent cases, advent of new technologies, etc. Furthermore, some particular terms may be arbitrarily selected by the applicant, and in this case, the meaning of the selected terms will be described in detail in the detailed description of the disclosure. Thus, the terms used herein should be defined not by simple appellations thereof but based on the meaning of the terms together with the overall description of the disclosure.

All the terms used herein, which include technical or scientific terms, may have the same meaning that is generally understood by a person of ordinary skill in the art. Although the terms including an ordinal number such as "first," "second," etc. may be used herein to describe various elements or components, these elements or components should not be limited by the terms. The terms are only used to distinguish one element or component from another element or component.

Throughout the specification, when a part "includes" or "comprises" an element, unless there is a particular description contrary thereto, it is understood that the part may further include other elements, not excluding the other elements. Furthermore, terms such as "portion," "module," etc. used herein indicate a unit for processing at least one function or operation and may be implemented as hardware or software or a combination of hardware and software.

Embodiments of the disclosure will now be described more fully hereinafter with reference to the accompanying drawings so that they may be easily implemented by one of ordinary skill in the art. However, the disclosure may be implemented in different forms and should not be construed as being limited to the embodiments set forth herein. In addition, parts not related to descriptions of the disclosure are omitted to clearly explain embodiments of the disclosure in the drawings, and like reference numerals denote like elements throughout.

In an embodiment of the disclosure, a contact pressure refers to a value of pressure at which a haptic actuator is in contact with a user of a wearable device so that the user may feel haptic feedback provided by the haptic actuator. Because sensing abilities of sensory organs in a body vary according to users, a contact pressure set so that a user may feel haptic feedback may be different for each user.

In an embodiment of the disclosure, a target contact pressure refers to a contact pressure value set for the user of the wearable device. The wearable device may determine a target contact pressure to be set for the user of the wearable device based on at least some of user profile data and data obtained from a sensor in the wearable device. In this case, the target contact pressure refers to a pressure set by the wearable device to provide haptic feedback to the user of the wearable device based on an appropriate contact pressure.

In an embodiment of the disclosure, biometric data refers to data obtained by a biosensor sensing biosignals generated in a user's body. For example, the biometric data may include at least one of a heart rate, a skin conductance response (SCR), or a skin temperature.

In an embodiment of the disclosure, user profile data refers to data regarding parameters related to the user's body. The user profile data may include data regarding at least one of gender, age, skin type (e.g., an oily skin, a dry skin, etc.), or body attributes (e.g., a height, a weight, etc.). The wearable device may receive the user profile data from the user or a server.

In an embodiment of the disclosure, information about an activity state refers to information indicating what a user's current activity is. The activity state may include, for example, normal, walking, running, etc., but is not limited thereto.

In an embodiment of the disclosure, information about a skin condition refers to information indicating a skin condition of the user of the wearable device. The skin condition may include, for example, whether the user sweats, whether foreign substances are on the skin, etc., but is not limited thereto.

Figure 1:
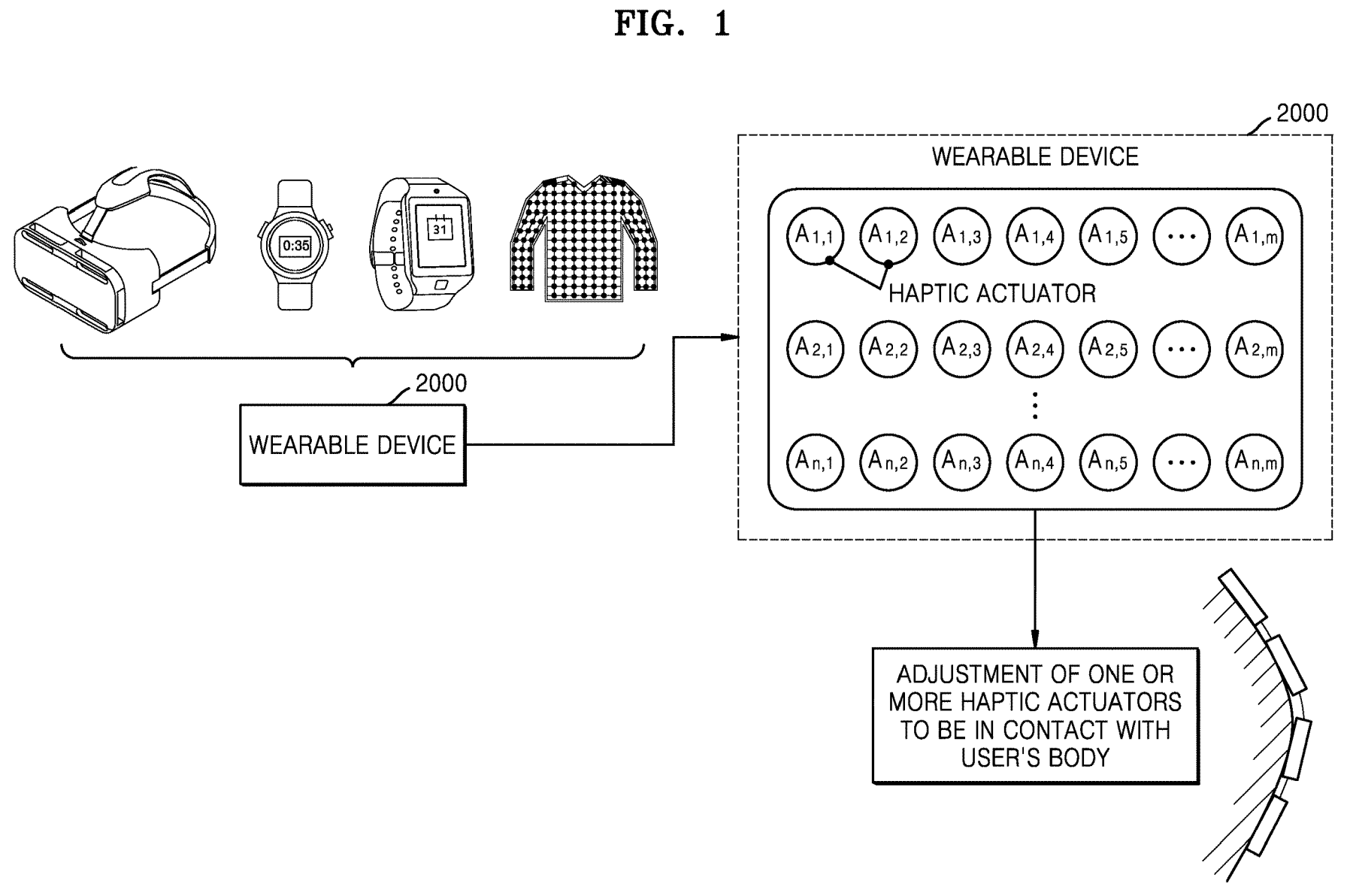

FIG. 1 is a diagram for describing wearable devices that provide haptic feedback, according to an embodiment of the disclosure.

Referring to FIG. 1, a wearable device 2000 according to an embodiment of the disclosure may provide haptic feedback to a user.

In an embodiment of the disclosure, the wearable device 2000 may include one or more haptic actuators. Examples of the wearable device 2000 may include a head-mounted display, a smart watch, a smart band, smart clothing, etc., but are not limited thereto.

In an embodiment of the disclosure, the degree of contact between the wearable device 2000 and the user may vary according to a method by which the user wears the wearable device 2000, a user's body structure, etc. The wearable device 2000 may identify a state in which the wearable device 2000 is worn by the user and control the wearable device 2000 so that a haptic actuator included in the wearable device 2000 is in contact with the user's body at a certain pressure.

In an embodiment of the disclosure, the degree of a user's perception of haptic feedback may be different for each user of the wearable device 2000 according to a contact pressure of the haptic actuator. For example, a contact pressure of the haptic actuator, a duration of the haptic feedback, a distance between haptic actuators, etc., for which the user is able to effectively sense haptic feedback, may be different for each user of the wearable device 2000. The wearable device 2000 may calculate a target contact pressure of a haptic actuator to allow the user to appropriately feel haptic feedback, based on sensor data obtained using sensors included in the wearable device 2000 and pieces of user profile information indicating a user's characteristics. For example, the wearable device 2000 may determine the target contact pressure based on user profile information (e.g., age, gender, height, weight, etc.), a user's skin condition, a user's activity state, etc.

In an embodiment of the disclosure, the wearable device 2000 may control a haptic actuator included therein to be in contact with a user's body based on a target contact pressure personalized for the user and thus adjust a contact pressure applied to the user's body by the haptic actuator.

In an embodiment of the disclosure, the wearable device 2000 may update the target contact pressure as a user's state (e.g., a skin condition and an activity state) changes while the user is wearing the wearable device 2000.

In an embodiment of the disclosure, the wearable device 2000 may update the target contact pressure when identifying that a user's skin condition has changed. The wearable device 2000 may identify that a user's skin condition has changed by identifying whether the user sweats, whether a foreign substance is on the skin, etc., and update the target contact pressure.

In an embodiment of the disclosure, the wearable device 2000 may update the target contact pressure when identifying that a user's activity state is changed. The wearable device 2000 may identify that a user's current activity (e.g., a normal state) is changed to another activity (e.g., a walking state) and update the target contact pressure.

When the target contact pressure is updated, the wearable device 2000 may control a haptic actuator included therein to be in contact with a user's body and thus adjust a contact pressure applied to the user's body by the haptic actuator.

In an embodiment of the disclosure, a structure in which a haptic actuator is mounted on the wearable device 2000 and a position of the haptic actuator in the wearable device 2000 may be different depending on a type of the wearable device 2000. To provide haptic feedback to the user based on the target contact pressure, the wearable device 2000 may include physical structures capable of adjusting a position of the haptic actuator to be closer to or farther away from the user's body.

Figure 2:
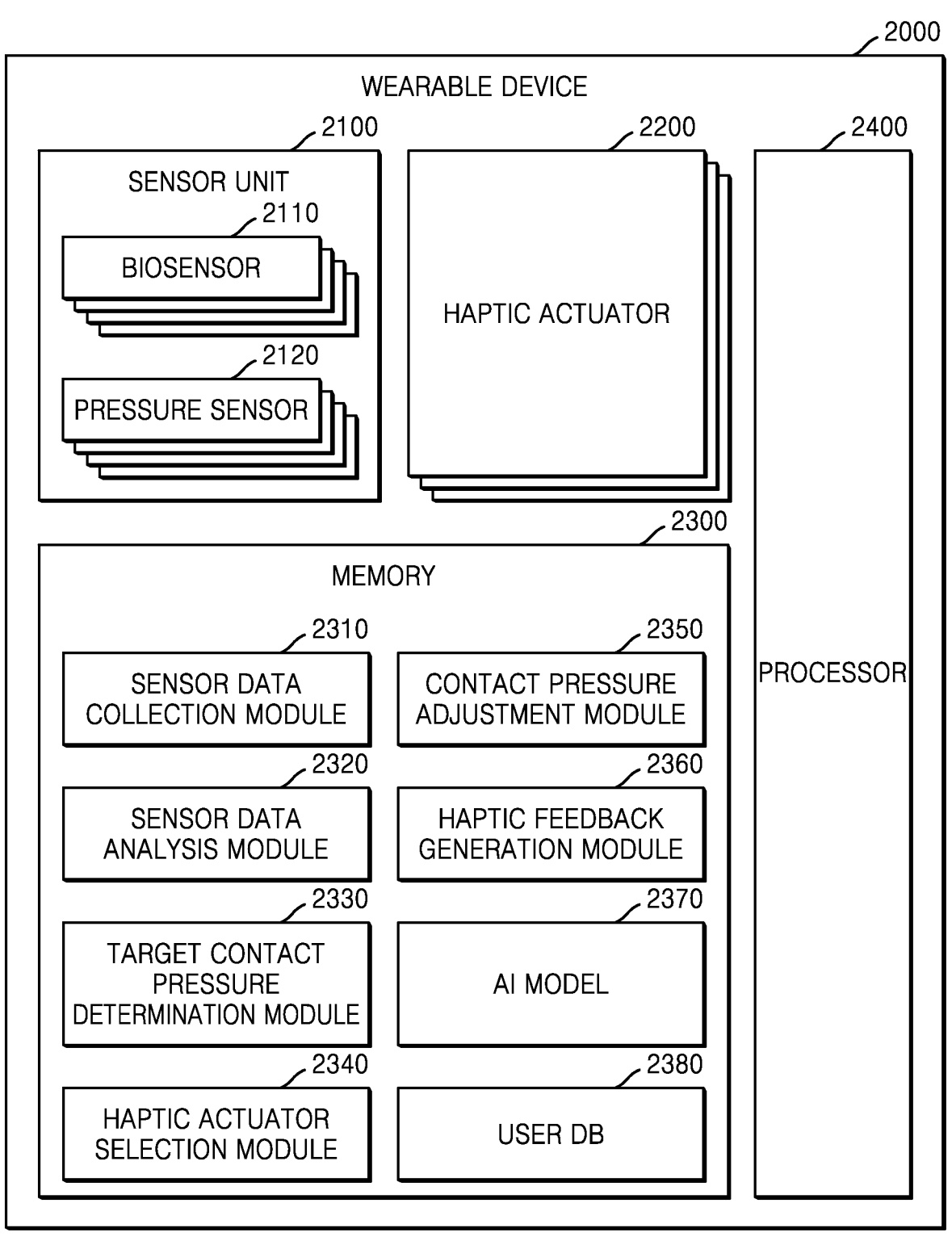
FIG. 2 is a block diagram of a configuration of a wearable device according to an embodiment of the disclosure.

FIG. 2 is a block diagram of a configuration of a wearable device according to an embodiment of the disclosure.

Referring to FIG. 2, a wearable device 2000 according to an embodiment of the disclosure may include a sensor unit 2100, one or more haptic actuators 2200, a memory 2300, and a processor 2400.

The sensor unit 2100 may include one or more biosensors 2110 for obtaining a user's biometric data and one or more pressure sensors 2120 for sensing a contact pressure of the haptic actuator 2200.

The biosensor 2110 may include at least one of an electrocardiography sensor, an electromyography sensor, a body temperature sensor, a skin resistance sensor, or a skin moisture sensor, but is not limited thereto. There may be one or more biosensors 2110.

The pressure sensor 2120 may include at least one of a piezoresistive tactile sensor, a piezoelectric tactile sensor, a capacitive tactile sensor, an optical tactile sensor, or an elastoresistive tactile sensor, but are not limited thereto. There may be one or more pressure sensors 2120. The pressure sensor 2120 may be placed between, for example, the haptic actuator 2200 to be described later and a user's body, and sense a contact pressure applied to the user by the haptic actuator 2200, but a position where the pressure sensor 2120 is placed is not limited thereto.

Furthermore, the sensor unit 2100 may include at least one of a geomagnetic sensor (not shown), an acceleration sensor (not shown), a temperature/humidity sensor (not shown), an infrared sensor (not shown), a gyroscope sensor (not shown), a position sensor (e.g., a global positioning system (GPS)) (not shown), a barometric pressure sensor (not shown), or a proximity sensor (not shown), but is not limited thereto.

Moreover, when a sensor included in the sensor unit 2100 is spaced apart from the user's body by a certain distance or greater and thus sensor data is not obtained, the wearable device 2000 may adjust a position of the sensor unit 2100 to be closer to the user's body until the sensor unit 2100 is able to obtain sensor data.

The haptic actuator 2200 may generate haptic feedback. Haptic feedback refers to feedback provided to a user so that the user may feel tactile sensations such as senses of force and movement via forces, vibrations, motions, etc. The haptic actuator 2200 may include at least one of a linear resonance actuator, an eccentric rotating mass actuator, a piezoelectric actuator, or a solenoid actuator, but is not limited thereto. There may be one or more haptic actuators 2200.

The memory 2300 may store instructions, data structures, and program code that are readable by the processor 2400. In the embodiments of the disclosure, operations performed by the processor 2400 may be implemented by executing instructions or code of a program stored in the memory 2300.

The memory 2300 may include a non-volatile memory including at least one of a flash memory-type memory, a hard disk-type memory, a multimedia card micro-type memory, a card-type memory (e.g., a secure digital (SD) card or an extreme digital (XD) memory), read-only memory (ROM), programmable ROM (PROM), electrically erasable PROM (EEPROM), a magnetic memory, a magnetic disk, or an optical disk, and a volatile memory such as random access memory (RAM) or static RAM (SRAM).

According to an embodiment of the disclosure, in order for the wearable device 2000 to determine a target contact pressure and provide haptic feedback, the memory 2300 may store various types of data that may be used to adjust a current contact pressure of the wearable device 2000 to equal the target contact pressure. For example, the memory 2300 may store data and program instruction codes corresponding to a sensor data collection module 2310, a sensor data analysis module 2320, a target contact pressure determination module 2330, a haptic actuator selection module 2340, a contact pressure adjustment module 2350, a haptic feedback generation module 2360, an artificial intelligence (AI) model 2370, and a user database (DB) 2380.

In an embodiment of the disclosure, the AI model 2370 may be trained based on a training dataset consisting of user profile data and biometric data obtained from the biosensor 2110.

In addition, the AI model 2370 may be trained to output a target contact pressure to be applied to a user's body by the haptic actuator 2200, based on a training dataset consisting of user profile data, data regarding a user's skin condition, and data regarding a user's activity state.

The AI model 2370 may include a plurality of neural network layers. Each of the plurality of neural network layers may include a plurality of nodes. In this case, a value of a node in a current layer may be a sum of results obtained by multiplying values of nodes in a previous layer by weight values. The AI model 2370 may update weight values indicating the strength of connection between nodes in neural network layers of the AI model 2370 by learning the training dataset. In addition, weight values for nodes in an input layer may include at least some of weight values corresponding to respective parameters (e.g., age, gender, body attributes, etc.) included in user profile data, weight values corresponding to respective parameters (e.g., a heart rate, an SCR, a skin temperature, etc.) included in biometric data, weight values corresponding to a user's skin condition, and weight values corresponding to a user's activity state.

By using the AI model 2370, the wearable device 2000 may output a target contact pressure value indicating a contact pressure to be applied to the user's body by the haptic actuator 2200 of the wearable device 2000.

In an embodiment of the disclosure, the wearable device 2000 may apply the user profile data and biometric data to the AI model 2370 and determine a target contact pressure value output from the AI model 2370.

In an embodiment of the disclosure, the wearable device 2000 may apply the user profile data, data regarding the user's skin condition, and data regarding the user's activity state to the AI model 2370 and determine a target contact pressure value output from the AI model 2370.

In an embodiment of the disclosure, the AI model 2370 may be generated by being trained in the wearable device 2000.

In an embodiment of the disclosure, the AI model 2370 may be generated via training in a server (not shown) and received and stored by the wearable device 2000.

In an embodiment of the disclosure, there may be one or more AI models 2370.

In an embodiment of the disclosure, the user DB 2380 may store sensor data obtained from the sensor unit 2100 and profile data obtained from the user.

The processor 2400 may control all operations of the wearable device 2000. For example, the processor 2400 may control all operations of the sensor unit 2100, the haptic actuator 2200, etc. by executing one or more instructions of a program stored in the memory 2300.

For example, the processor 2400 may include, but is not limited thereto, at least one of a central processing unit (CPU), a microprocessor, a graphics processing unit (GPU), application specific integrated circuits (ASICs), digital signal processors (DSPs), digital signal processing devices (DSPDs), programmable logic devices (PLDs), field programmable gate arrays (FPGAs), an application processor (AP), a neural processing unit (NPU), or a dedicated AI processor designed with a hardware structure specialized for processing an AI model.

In an embodiment of the disclosure, the processor 2400 may execute the sensor data collection module 2310 to obtain pieces of sensor data detected by the sensor unit 2100.

In an embodiment of the disclosure, the processor 2400 may execute the sensor data collection module 2310 to obtain biometric data that is sensor data detected by the biosensor 2110. In this case, the biometric data may include at least one of a heart rate, an SCR, or a skin temperature.

In an embodiment of the disclosure, the processor 2400 may execute the sensor data collection module 2310 to obtain contact pressure data that is sensor data detected by the pressure sensor 2120.

Pieces of sensor data collected in real-time using the sensor data collection module 2310 may be analyzed and used by the processor 2400 to determine an operation of the wearable device 2000. Furthermore, the processor 2400 may store the collected pieces of sensor data in the user DB 2380.

In an embodiment of the disclosure, the processor 2400 may execute the sensor data analysis module 2320 to analyze the collected pieces of sensor data.

In an embodiment of the disclosure, the processor 2400 may execute the sensor data analysis module 2320 to identify whether the user wears the wearable device 2000. The processor 2400 may analyze the biometric data and the contact pressure data obtained in real-time to identify whether the user wears the wearable device 2000. For example, when at least one of the biometric data or the contact pressure data is obtained, the processor 2400 may determine that the user wears the wearable device 2000. As another example, the processor 2400 may determine that the user wears the wearable device 2000 based on a combination of at least some of the biometric data and the contact pressure data. As another example, the processor 2400 may determine that the user wears the wearable device 2000 based on sensor data obtained from other sensors such as an infrared sensor and a proximity sensor.

In an embodiment of the disclosure, the processor 2400 may execute the sensor data analysis module 2320 to identify a skin condition of the user wearing the wearable device 2000. The processor 2400 may identify the user's skin condition based on an SCR, a skin temperature, etc. included in the biometric data. In this case, the user's skin condition may include various pieces of information indicating the user's skin condition, such as a skin type (e.g., an oily skin, a dry skin, etc.), a skin moisture level, etc.

In an embodiment of the disclosure, the processor 2400 may execute the sensor data analysis module 2320 to identify an activity state of the user wearing the wearable device 2000. In this case, the user's activity state may include, but is not limited to, normal, walking, running, etc.

For example, the processor 2400 may identify the user's activity state based on an SCR, a skin temperature, a heart rate, etc. included in the biometric data obtained from the biosensor 2110. As another example, the processor 2400 may identify the user's activity state based on values sensed using an acceleration sensor, a gyro sensor, etc. As another example, the processor 2400 may identify the user's activity state based on sensor data obtained from at least one of the biosensor 2110, an acceleration sensor, or a gyro sensor.

In an embodiment of the disclosure, the processor 2400 may execute the target contact pressure determination module 2330 to calculate a target contact pressure.

The processor 2400 may execute the target contact pressure determination module 2330 to determine the target contact pressure based on the user profile data and the biometric data. In this case, the user's skin condition identified based on the biometric data according to the embodiments of the disclosure and the user's activity state identified based on at least some of the biometric data, acceleration sensor data, and gyro sensor data according to the embodiments of the disclosure may be used when determining the target contact pressure. Furthermore, the user profile data may be prestored in the user DB 2380.

In an embodiment of the disclosure, the processor 2400 may determine a target contact pressure by using the target contact pressure determination module 2330 and the AI model 2370, i.e., by applying the user profile data, the user's skin condition, and the user's activity state to the AI model 2370. In this case, the AI model 2370 may be an AI model that receives the user profile data and biometric data and is trained based thereon to output a target contact pressure value. In addition, the AI model 2370 may be an AI model that receives the user profile data, data regarding the user's skin condition, and data regarding the user's activity state and is trained based thereon to output a target contact pressure value.

The processor 2400 may control the haptic actuator 2200 to be in contact with the user's body based on the target contact pressure and provide haptic feedback.

In an embodiment of the disclosure, the processor 2400 may identify that a user's skin condition has changed, and change a target contact pressure value due to the change in the user's skin condition. For convenience of description, a target contact pressure value changed by the processor 2400 due to a change in a user's skin condition will hereinafter be referred to as a first target contact pressure.

The processor 2400 may identify that the user's skin condition has changed based on an SCR, a skin temperature, etc. included in biometric data obtained from the biosensor 2110. For example, the processor 2400 may identify that the user's skin condition has changed by identifying whether the user sweats, whether foreign substances are on the skin, etc., based on the biometric data. The processor 2400 may determine a first target contact pressure by applying the changed skin condition, the user profile data, and the user's activity state to the AI model 2370, and change a target contact pressure value of the haptic actuator 2200 to the first target contact pressure. The processor 2400 may continuously recalculate and update the first target contact pressure based on the user's biometric data continuously obtained from the biosensor 2110.

The processor 2400 may control the haptic actuator 2200 to be in contact with the user's body based on the first target contact pressure and provide haptic feedback.

In an embodiment of the disclosure, the processor 2400 may identify that a user's activity state is changed and change a target contact pressure value due to the change in the user's activity state. For convenience of description, a target contact pressure value changed by the processor 2400 due to a change in a user's activity state will hereinafter be referred to as a second target contact pressure.

The processor 2400 may identify that the user's activity state is changed based on at least one of biometric data obtained from the biosensor 2110, acceleration sensor data, or gyro sensor data. In this case, the processor 2400 may identify that the user's activity state is changed from a first activity state to a second activity state based on at least one of the biometric data, the acceleration sensor data, or the gyro sensor data. For example, the processor 2400 may identify that the user's activity state has changed from 'normal' to 'running'.

When it is identified that the user's activity state is changed, the processor 2400 may calculate a second target contact pressure based on the degree of a change in the first target contact pressure until the user's activity state is changed. The processor 2400 may change the first target contact pressure to the second target contact pressure.

In an embodiment of the disclosure, when the user's activity state is changed from the first activity state to the second activity state, the processor 2400 may calculate the second target contact pressure based on a mean of first target contact pressures changed over a certain time duration and a standard deviation of the first target contact pressures. For example, the processor 2400 may determine the second target contact pressure by calculating a sum of the mean of the first target contact pressures that have been changed for the certain time duration and the standard deviation of the first target contact pressures.

The processor 2400 may control the haptic actuator 2200 to be in contact with the user's body based on the second target contact pressure and provide haptic feedback.

In an embodiment of the disclosure, when a target contact pressure is changed to the second target contact pressure as the user's activity changes from the first activity state to the second activity state, the processor 2400 may identify that the user's skin condition has changed again when the user's activity is in the second activity state. The processor 2400 may change again the target contact pressure value that has been changed to the second target contact pressure due to the change in the user's skin condition. Because the method, performed by the processor 2400, of changing a target contact pressure value due to a change in the user's skin condition has been described above, a detailed description thereof will be omitted.

In an embodiment of the disclosure, the processor 2400 may identify that the user's activity state is changed to another activity state. For example, the processor 2400 may identify that the user's activity state is changed from the second activity state to a third activity state. The processor 2400 may change again the target contact pressure value that has been changed to the second target contact pressure due to the change in the user's activity state. Because the method, performed by the processor 2400, of changing a target contact pressure value due to a change in the user's activity state has been described above, a detailed description thereof will be omitted.

In an embodiment of the disclosure, there may be a plurality of haptic actuators 2200. In this case, target contact pressures may respectively correspond to the plurality of haptic actuators 2200. The processor 2400 may calculate, for each of the plurality of haptic actuators 2200, a target contact pressure corresponding thereto. Furthermore, for each of the plurality of haptic actuators 2200, the processor 2400 may identify that the user's skin condition has changed and change a target contact pressure value corresponding to each of the haptic actuators 2200. In addition, for each of the plurality of haptic actuators 2200, the processor 2400 may identify that the user's activity state is changed and change a target contact pressure value corresponding to each of the plurality of the haptic actuators 2200.

In an embodiment of the disclosure, the processor 2400 may execute the haptic actuator selection module 2340 to determine the haptic actuator 2200 that has a current contact pressure to be adjusted. In an embodiment of the disclosure, there may be one or more haptic actuators 2200.

In an embodiment of the disclosure, when the wearable device 2000 includes only one haptic actuator 2200, the processor 2400 may compare a target contact pressure of the haptic actuator 2200 with a current contact pressure thereof in order to adjust the current contact pressure of the haptic actuator 2200.

In an embodiment of the disclosure, when the wearable device 2000 includes a plurality of haptic actuators 2200, the processor 2400 may compare, for each of the plurality of haptic actuators 2200, a target contact pressure of the corresponding haptic actuator 2200 with a current target contact pressure thereof to thereby select a haptic actuator that has a current contact pressure to be adjusted from among the plurality of haptic actuators 2200.

In an embodiment of the disclosure, the processor 2400 may execute the contact pressure adjustment module 2350 to adjust a current contact pressure of the haptic actuator 2200. The processor 2400 may obtain a current contact pressure applied to the user's body by the haptic actuator 2200 and measured using the pressure sensor 2120. The processor 2400 may adjust the current contact pressure of the haptic actuator 2200 to equal a target contact pressure.

For example, when the current contact pressure of the haptic actuator 2200 is less than the target contact pressure, the processor 2400 may adjust a position of the haptic actuator 2200 to be closer to the user's body so that the current contact pressure increases up to the target contact pressure.

As another example, when the current contact pressure of the haptic actuator 2200 is greater than the target contact pressure, the processor 2400 may adjust the position of the haptic actuator 2200 to be farther away from the user's body so that the current contact pressure decreases to the target contact pressure.

In an embodiment of the disclosure, the operation of the processor 2400 adjusting the current contact pressure of the haptic actuator 2200 by executing the contact pressure adjustment module 2350 may be performed differently depending on a type of the wearable device 2000 (e.g., a smart watch, smart clothing, a head-mounted display, etc.). In addition, the operation of the processor 2400 adjusting the current contact pressure of the haptic actuator 2200 by executing the contact pressure adjustment module 2350 may be performed differently depending on a method by which the haptic actuator 2200 is mounted on the wearable device 2000 (e.g., a method using a fluid pump, a method using gears, etc.).

A detailed method, performed by the processor 2400, of adjusting a position of the haptic actuator 2200 so that it is closer to or farther away from a user's body in order to adjust a current contact pressure of the haptic actuator 2200 by executing the contact pressure adjustment module 2350 will be described below with reference to FIGS. 17A, 17B, 17C, 18A, 18B, and 19.

In an embodiment of the disclosure, the processor 2400 may control the haptic actuator 2200 to generate haptic feedback by executing the haptic feedback generation module 2360.

In an embodiment of the disclosure, haptic feedback refers to feedback provided to the user so that the user may feel tactile sensations such as senses of force and movement via various types of forces, vibrations, and motions. The processor 2400 may convert a target contact pressure value into a value expressed in another measurement unit indicating a force capable of transmitting a tactile sensation to the user. For example, the processor 2400 may convert a target contact pressure value into a value expressed in a measurement unit such as hertz (Hz) or amperes (A), but is not limited thereto.

The processor 2400 may adjust intensity of haptic feedback delivered to the user by using a pulse width modulation (PWM) technique. In this case, the processor 2400 may match the target contact pressure value that is converted into a value in another measurement unit (e.g., hertz (Hz), amperes (A), etc.) with a minimum output voltage for the wearable device 2000, such that a minimum intensity of the haptic feedback provided by the wearable device 2000 equals an intensity corresponding to the target contact pressure value.

Figure 3:
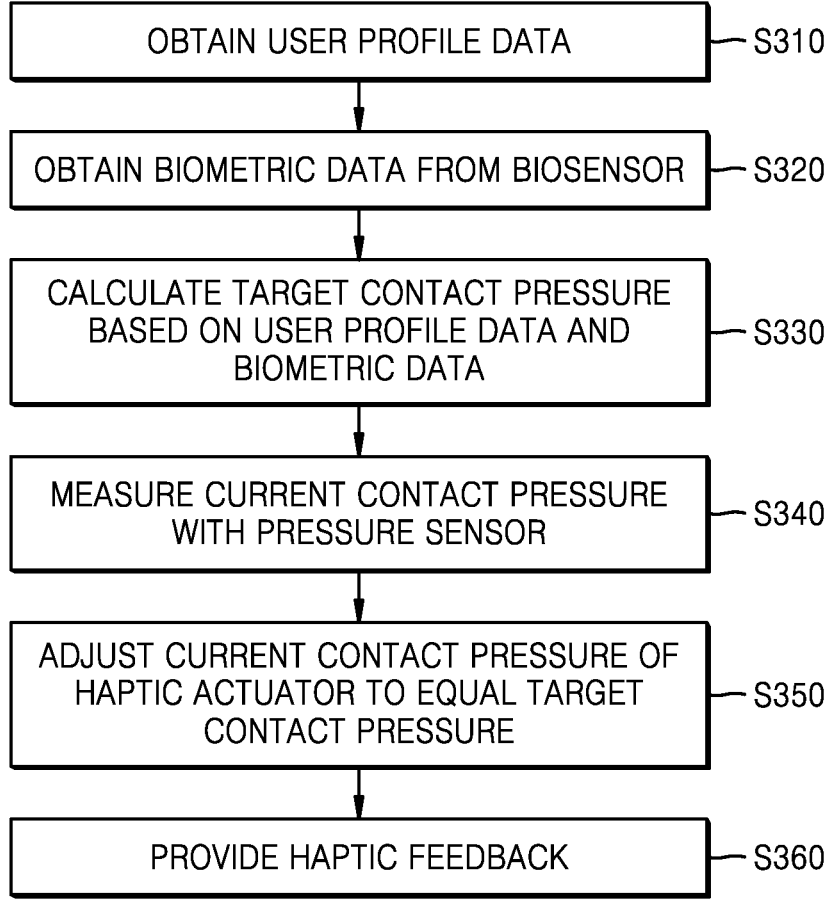
FIG. 3 is a flowchart of a method, performed by a wearable device, of providing haptic feedback, according to an embodiment of the disclosure.

FIG. 3 is a flowchart of a method, performed by a wearable device, of providing haptic feedback, according to an embodiment of the disclosure.

Referring to FIG. 3, according to an embodiment of the disclosure, in operation S310, the wearable device 2000 may obtain user profile data. The user profile data is data corresponding to parameters related to a user's body and may include at least one of gender, age, skin type (e.g., an oily skin, a dry skin, etc.), or body attributes (e.g., a height, a weight, etc.). The wearable device 2000 may receive the user profile data from the user or a server.

According to an embodiment of the disclosure, in operation S320, the wearable device 2000 may obtain biometric data from a biosensor. The biometric data is data obtained by the biosensor sensing biosignals originating from the user's body and may include at least one of a heart rate, an SCR, or a skin temperature. The wearable device 2000 may monitor biosignals from the user's body by using the biosensor, and continuously obtain biometric data.

In an embodiment of the disclosure, there may be a plurality of biosensors. In this case, the number of biosensors may correspond to the number of haptic actuators. The wearable device 2000 may obtain pieces of biometric data by measuring biosignals from different parts of the user's body by using the plurality of biosensors.

According to an embodiment of the disclosure, in operation S330, the wearable device 2000 may calculate a target contact pressure based on the user profile data and the biometric data.

In an embodiment of the disclosure, the wearable device 2000 may determine a target contact pressure based on the user profile data and biometric data. The wearable device 2000 may apply the user profile data and biometric data to an AI model and determine a target contact pressure value output from the AI model.

In an embodiment of the disclosure, when a plurality of haptic actuators are included in the wearable device 2000, the wearable device 2000 may determine a target contact pressure for each of the plurality of haptic actuators.

According to an embodiment of the disclosure, in operation S340, the wearable device 2000 may measure a current contact pressure applied to the user's body by a haptic actuator by using a pressure sensor. By using the pressure sensor, the wearable device 2000 may monitor a pressure at which a haptic actuator is in contact with the user's body, and continuously obtain contact pressure data.

In an embodiment of the disclosure, the number of pressure sensors included in the wearable device 2000 may correspond to the number of haptic actuators. For example, when a plurality of haptic actuators are included in the wearable device 2000, the wearable device 2000 may include a plurality of pressure sensors respectively corresponding to the plurality of haptic actuators. In this case, each of the plurality of pressure sensors may monitor a pressure at which a corresponding one of the plurality of haptic actuators is in contact with the user's body, and continuously obtain contact pressure data.

According to an embodiment of the disclosure, in operation S350, the wearable device 2000 may adjust the current contact pressure of the haptic actuator, which is measured in operation S340, to equal the target contact pressure.

In an embodiment of the disclosure, the wearable device 2000 may compare the target contact pressure of the haptic actuator with the current contact pressure thereof to adjust the current contact pressure of the haptic actuator.

In some embodiment of the disclosure, when the current contact pressure of the haptic actuator included in the wearable device 2000 is less than the target contact pressure, the wearable device 2000 may adjust a position of the haptic actuator to be closer to the user's body so that the current contact pressure increases up to the target contact pressure. In some embodiment of the disclosure, when the current contact pressure of the haptic actuator is greater than the target contact pressure, the wearable device 2000 may adjust the position of the haptic actuator to be farther away from the user's body so that the current contact pressure decreases to the target contact pressure.

In an embodiment of the disclosure, a plurality of haptic actuators may be included in the wearable device 2000. When the plurality of haptic actuators are included in the wearable device 2000, the wearable device 2000 may compare, for each of the plurality of haptic actuators, a target contact pressure of the corresponding haptic actuator with a current target contact pressure thereof to thereby select a haptic actuator that has a current contact pressure to be adjusted from among the plurality of haptic actuators. The wearable device 2000 may adjust a position of each of the plurality of haptic actuators so that a current contact pressure of the haptic actuator becomes equal to a target contact pressure corresponding to each of the plurality of haptic actuators.

According to an embodiment of the disclosure, in operation S360, the wearable device 2000 may provide haptic feedback to the user by using a haptic actuator that is in contact with the user's body to have a target contact pressure value. The wearable device 2000 may control the haptic actuator to generate haptic feedback so that the user may feel tactile sensations such as senses of force and movement.

In an embodiment of the disclosure, the wearable device 2000 may adjust intensity of haptic feedback delivered to the user by using a PWM technique. In this case, the wearable device 2000 may convert a target contact pressure value into a value expressed in another measurement unit (e.g., hertz (Hz), amperes (A), etc.) indicating a force capable of transmitting a tactile sensation to the user. The wearable device 2000 may match the target contact pressure value that is converted into a value in another measurement unit with a minimum output voltage for the wearable device 2000, such that a minimum intensity of the haptic feedback provided by the wearable device 2000 equals an intensity corresponding to the target contact pressure value.

FIG. 4 is a flowchart of a method, performed by a wearable device, of determining a target contact pressure, according to an embodiment of the disclosure.

Referring to FIG. 4, operations S310, S320, and S330 of the wearable device 2000 illustrated in FIG. 3 are now described in more detail.

According to an embodiment of the disclosure, in operation S410, the wearable device 2000 may identify whether a user wears the wearable device 2000.

For example, when at least one of biometric data or contact pressure data is obtained from a biosensor or pressure sensor, the wearable device 2000 may determine that the user wears the wearable device 2000 itself. As another example, the wearable device 2000 may determine that the user wears the wearable device 2000 itself based on a combination of at least some of biometric data obtained from a biosensor and contact pressure data obtained from a pressure sensor. As another example, the wearable device 2000 may determine that the user wears the wearable device 2000 itself based on sensor data obtained from other sensors such as an infrared sensor, a proximity sensor, etc. As another example, the wearable device 2000 may determine that the user wears the wearable device 2000 itself based on at least some of sensor data obtained from a biosensor, a pressure sensor, an infrared sensor, a proximity sensor, etc. Operation S410 may be performed after operations S310 and S320 of FIG. 3 are performed.

In operation S420, the wearable device 2000 may determine which operation to perform based on whether the user wears the wearable device 2000.

In an embodiment of the disclosure, when it is not identified that the user wears the wearable device 2000, the wearable device 2000 may monitor whether the user wears the wearable device 2000 itself by repeatedly performing operation S410 until it is identified that the user wears the wearable device 2000.

In an embodiment of the disclosure, when it is identified that the user wears the wearable device 2000, the wearable device 2000 may perform operation S430.

According to an embodiment of the disclosure, in operation S430, the wearable device 2000 may collect biometric data and user profile data.

The wearable device 2000 may receive user profile data from the user or a server, or obtain user profile data stored in the wearable device 2000 itself.

When it is identified that the user wears the wearable device 2000, the wearable device 2000 may monitor the user's bio-signals that change in real-time via a biosensor, and continuously obtain biometric data.

According to an embodiment of the disclosure, in operation S440, the wearable device 2000 may identify a user's skin condition based on the biometric data. The wearable device 2000 may identify the user's skin condition based on an SCR, a skin temperature, etc., included in the biometric data. In this case, the user's skin condition may include various pieces of information indicating the user's skin condition, such as a skin type (e.g., an oily skin, a dry skin, etc.), a skin moisture level, etc.

According to an embodiment of the disclosure, in operation S450, the wearable device 2000 may identify a user's activity state based on sensor data. In this case, the sensor data may include, but is not limited to, biometric data obtained from a biosensor, acceleration data obtained from an acceleration sensor, angular velocity data obtained from a gyro sensor, etc. Furthermore, the user's activity state may include normal, walking, running, etc., but is not limited thereto.

In an embodiment of the disclosure, the wearable device 2000 may identify the user's activity state based on an SCR, a skin temperature, a heart rate, etc. included in the biometric data. For example, the wearable device 2000 may identify whether the user is in a normal state, walking, running, etc., based on an SCR, a skin temperature, a heart rate, etc.

In an embodiment of the disclosure, the wearable device 2000 may identify the user's activity state based on values sensed using an acceleration sensor, a gyro sensor, etc. For example, the wearable device 2000 may identify whether the user is in a normal state, walking, running, etc. based on an acceleration, an angular velocity, etc., with which the user moves.

In an embodiment of the disclosure, the wearable device 2000 may determine the user's activity state based on a combination of at least some of pieces of sensor data obtained from a biosensor, an acceleration sensor, and a gyro sensor.

According to an embodiment of the disclosure, in operation S460, the wearable device 2000 may determine a target contact pressure based on the user profile data, the user's skin condition, the user's activity state, etc.

According to an embodiment of the disclosure, the wearable device 2000 may apply the user profile data, the user's skin condition, and the user's activity state to an AI model and determine a target contact pressure output from the AI model.

After operation S460 is performed, operations S340, S350 and S360 of FIG. 3 may be performed.

Figure 5:
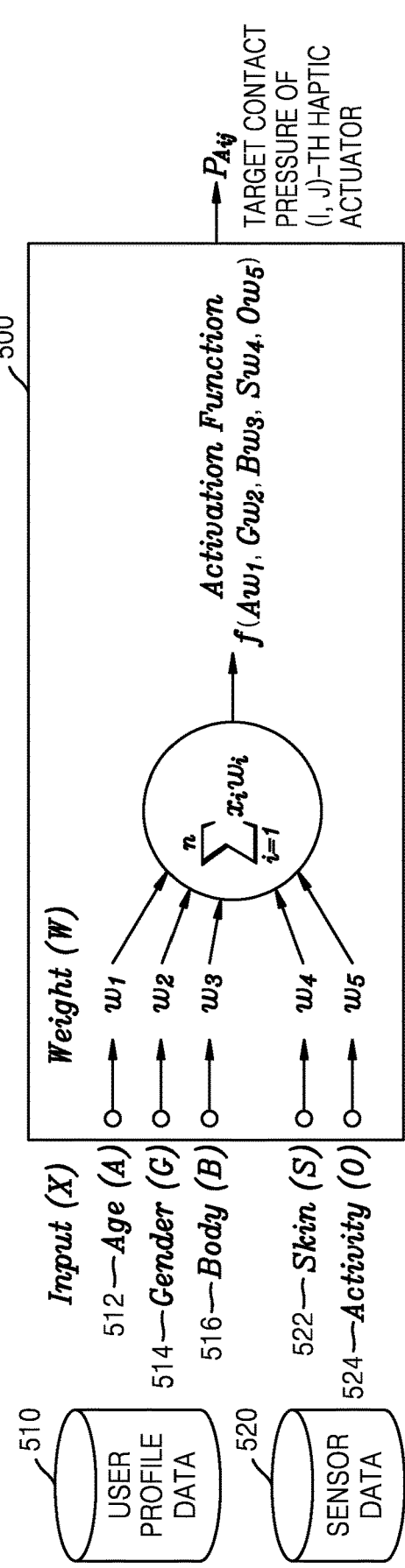
FIG. 5 is a diagram for describing a method, performed by a wearable device, of determining a target contact pressure, according to an embodiment of the disclosure.

FIG. 5 is a diagram for describing a method, performed by a wearable device, of determining a target contact pressure, according to an embodiment of the disclosure.

Referring to FIG. 5, according to an embodiment of the disclosure, the wearable device 2000 may determine a target contact pressure of a haptic actuator by using an AI model 500.

According to an embodiment of the disclosure, the wearable device 2000 may obtain user profile data 510. The user profile data 510 may include at least one of a user's gender, age, skin type (e.g., an oily skin, a dry skin, etc.), or body attributes (e.g., a height, a weight, etc.). The wearable device 2000 may receive the user profile data 510 from the user via a user input interface included therein. Furthermore, the wearable device 2000 may obtain the user profile data 510 prestored therein. In this case, the user profile data 510 may be received from another electronic device interworking with the wearable device 2000 or from a server.

According to an embodiment of the disclosure, the wearable device 2000 may obtain sensor data 520. In this case, the sensor data may include at least one of biometric data obtained from a biosensor, acceleration data obtained from an acceleration sensor, or angular velocity data obtained from a gyro sensor. The wearable device 2000 may obtain data regarding a user's skin condition and data regarding a user's activity state based on the sensor data 520. Because these have been described in conjunction with the embodiments of the disclosure, descriptions thereof will be omitted below.

The AI model 500 may include a plurality of neural network layers. Each of the plurality of neural network layers may include a plurality of nodes. The AI model 500 may receive the user profile data 510, data regarding the user's skin condition, and data regarding the user's activity state.

For example, the wearable device 2000 may input, to the AI model 500, age (A) 512, gender (G) 514, and body attributes (B) 516 as input data, which are data included in the user profile data 510.

In addition, the wearable device 2000 may input, to the AI model 500, a skin condition (S) 522 and an activity state (O) 524 as input data, which are data obtained based on the sensor data 520.

The AI model 500 may perform multiplication and summation operations of multiplying weights by values of nodes in each of the plurality of neural network layers and adding results of the multiplications. In this case, a value of a node in a current layer may be a sum of results obtained by multiplying values of nodes in a previous layer by weight values. In this case, a value of node k in layer N that is a current layer may be expressed using Equation 1 below.

$$node_k = \sum\nolimits_{i=1}^{n} (x_i w_i) \qquad \text{Equation 1}$$

where $x_i$ denotes a value of node i in layer N−1 that is a previous layer, and $w_i$ denotes a weight indicating the strength of connection between 'node i' in 'layer N−1' that is the previous layer and 'node k' in 'layer N' that is the current layer.

The AI model 500 may use an activation function in at least some of the plurality of neural network layers to output a result of calculation. For example, an activation function used in the input layer may be expressed using Equation 2 below.

$$f(A\overline{\omega}_1, G\overline{\omega}_2, B\overline{\omega}_3, S\overline{\omega}_4, O\overline{\omega}_5 s) \qquad \text{Equation 2}$$

where A, G, B, S, and O respectively denote age, gender, body attributes, a skin condition, and an activity state, and $\overline{\omega}_1$, $\vec{\omega}_2$, $\overline{\omega}_3$, $\overline{\omega}_4$, and $\overline{\omega}_5$ denote weights respectively corresponding to A, G, B, S, and O.

In an embodiment of the disclosure, an activation function used by the AI model 500 may include a sigmoid function, a rectified linear unit (ReLU) function, a hyperbolic tangent (tanh) function, etc., but is not limited thereto.

In an embodiment of the disclosure, the wearable device 2000 may output a target contact pressure value by inputting the user profile data 510, the data regarding the user's skin condition, and the data regarding the user's activity state to the AI model 500.

In an embodiment of the disclosure, when a plurality of haptic actuators are included in the wearable device 2000, the wearable device 2000 may determine a target contact pressure for each of the plurality of haptic actuators by using the AI model 500. For example, the wearable device 2000 may determine a target contact pressure value $P_{A_{ij}}$ for an (i, j)-th haptic actuator $A_{i,j}$.

Figure 6:
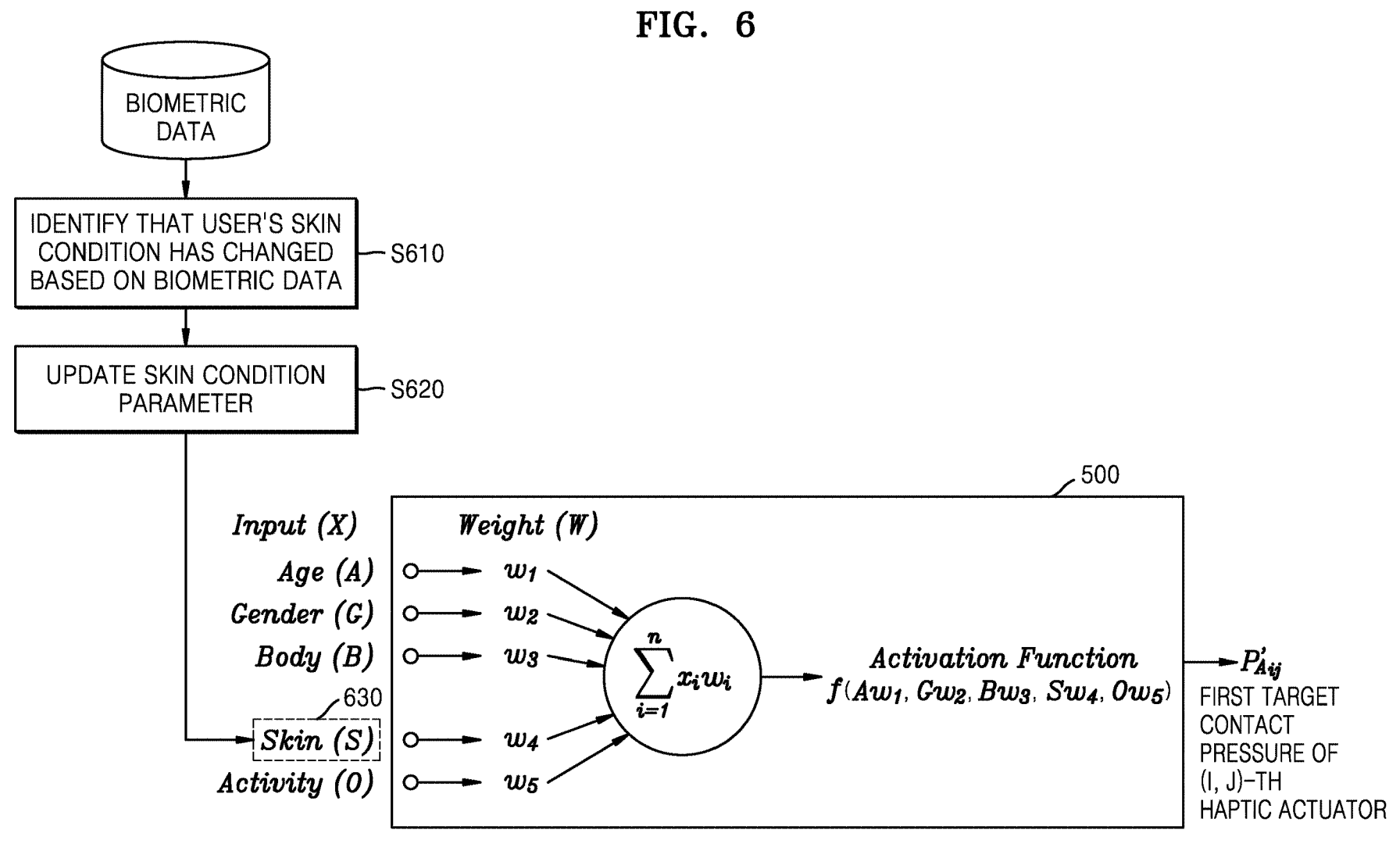

FIG. 6 is a diagram for describing a method, performed by a wearable device, of identifying a change in a skin condition and determining a first target contact pressure, according to an embodiment of the disclosure.

Referring to FIG. 6, according to an embodiment of the disclosure, in operation S610, the wearable device 2000 may identify whether a user's skin condition has changed based on biometric data obtained from a biosensor.

For example, the wearable device 2000 may identify that the user's skin condition has changed from a normal state to a sweating state based on at least some of an SCR and a skin temperature included in the biometric data. In this case, due to sweat on the user's skin, haptic feedback may not be properly provided by a haptic actuator, and thus a target contact pressure may need to be updated.

According to an embodiment of the disclosure, in operation S620, when it is identified that the user's skin condition has changed, the wearable device 2000 may update a value of a skin condition parameter 630 corresponding to the user's skin condition. For example, the wearable device 2000 may identify that the user's skin condition has changed from a normal state to a sweating state, and change the value of the skin condition parameter 630 to a value corresponding to the sweating state. In this case, the wearable device 2000 may adjust the value of the skin condition parameter 630 within a preset range based on the degree to which the user sweats.

The wearable device 2000 may newly calculate a target contact pressure value of the haptic actuator based on the updated value of the skin condition parameter 630. Furthermore, the wearable device 2000 may continuously update a target contact pressure value of the haptic actuator each time the value of the user's skin condition parameter 630 changes. In an embodiment of the disclosure, target contact pressure values newly calculated by the wearable device 2000 as the user's skin condition changes will be referred to as a first target contact pressure.

In an embodiment of the disclosure, the wearable device 2000 may input user profile data, data regarding the user's skin condition, and data regarding a user's activity state to an AI model 600, and output a first target contact pressure. In this case, the data regarding the user's skin condition may be the updated value of the skin condition parameter 630.

In an embodiment of the disclosure, when a plurality of haptic actuators are included in the wearable device 2000, the wearable device 2000 may determine a first target contact pressure for each of the plurality of haptic actuators by using the AI model 600. For example, the wearable device 200 may determine a first target contact pressure $P'_{A_{i,j}}$ for an (i, j)-th haptic actuator $A_{i,j}$.

Because the method, performed by the wearable device 2000, of determining a first target contact pressure by using the AI model 500 corresponds to the method of determining a target contact pressure, which has been described with reference to FIG. 5, a detailed description thereof will be omitted.

Figure 7:
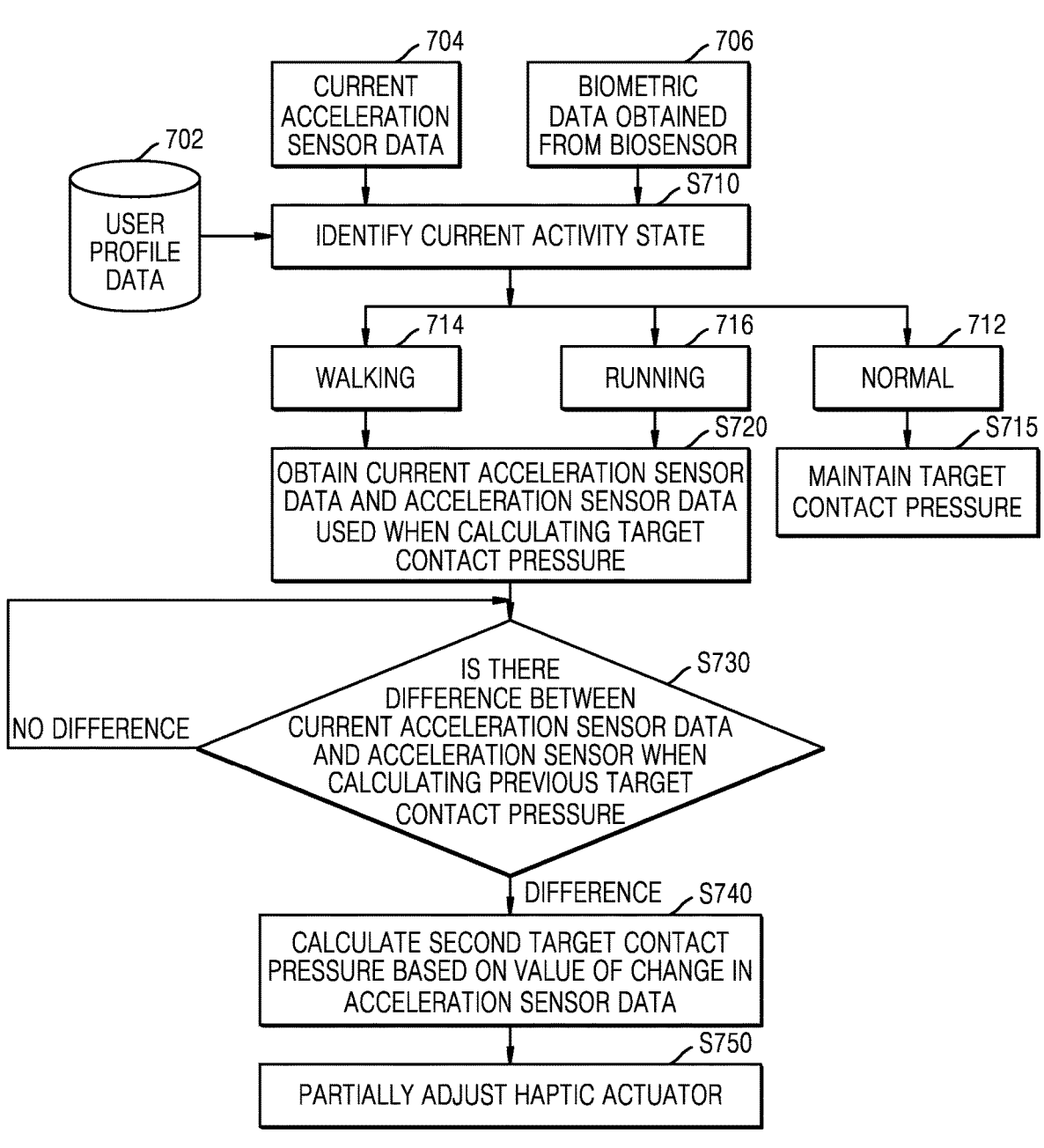
FIG. 7 is a flowchart of a method, performed by a wearable device, of adjusting a position of haptic actuator by analyzing a user's activity state, according to an embodiment of the disclosure.

FIG. 7 is a flowchart of a method, performed by a wearable device, of adjusting a position of a haptic actuator by analyzing a user's activity state, according to an embodiment of the disclosure.

Referring to FIG. 7, according to an embodiment of the disclosure, in operation S710, the wearable device 2000 may identify a user's current activity state. The wearable device 2000 may identify a user's activity state based on at least some of user profile data 702, current acceleration sensor data 704, and biometric data 706 obtained from a biosensor. For example, the wearable device 2000 may identify that the user's current activity state is a normal state 712, a walking state 714, a running state 716, or the like, but the user's activity state is not limited thereto.

Operation S710 may be performed after the wearable device 2000 determines a target contact pressure by performing operation S330 of FIG. 3 or operation S460 of FIG. 4.

For convenience of description, an example in which operation S330 of FIG. 3 and operation S460 of FIG. 4 are performed by the wearable device 2000 to determine a target contact pressure in advance, and the user's activity state was normal when the wearable device 2000 previously determined the target contact pressure will be described below.

The wearable device 2000 may identify the user's current activity state (e.g., the normal state 712, the walking state 714, and the running state 716) based on at least some of the user profile data 702, the current acceleration sensor data 704, and the biometric data 706 obtained from the biosensor.

When the user's current activity state is identified as the normal state 712, the wearable device 2000 may perform operation S715. Furthermore, when the user's current activity state is identified as the walking state 714 or running state 716, the wearable device 2000 may perform operation S720.

In operation S715, the wearable device 2000 may maintain a previously determined target contact pressure value without changing it. The wearable device 2000 may maintain the previous target contact pressure value because the 'normal state 712' that is the identified user's current activity state is the same as the user's previous activity state (normal state).

In operation S720, the wearable device 2000 may obtain acceleration sensor data used when the wearable device 2000 previously calculated the target contact pressure and current acceleration sensor data 704. When the user's current activity state is identified as the walking state 714 or running state 716, because the identified user's current activity state 'the walking state 714' or 'the running state 716' is different from the user's previous activity state (normal state), the wearable device 2000 may update a target contact pressure value in order to provide a target contact pressure suitable for the changed user's activity state.

In operation S730, the wearable device 2000 may identify whether a difference exists between the current acceleration sensor data 704 and the acceleration sensor data used when calculating the previous target contact pressure. When a difference exists between the current acceleration sensor data 704 and the acceleration sensor data used when calculating the previous target contact pressure, the wearable device 2000 may perform operation S740. When no difference exists therebetween, the wearable device 2000 may repeatedly perform operation S730.

In operation S740, the wearable device 2000 may calculate a value of change in acceleration sensor data. The wearable device 2000 may calculate a second target contact pressure based on the value of change in the acceleration sensor data. In this case, the second target contact pressure refers to target contact pressure values newly calculated by the wearable device 2000 as the user's activity state is changed. The wearable device 2000 may continuously update a target contact pressure value of a haptic actuator each time it is identified that the user's activity state is changed. A method, performed by the wearable device 2000, of calculating the second target contact pressure will be further described with reference to FIG. 8.

In operation S750, the wearable device 2000 may adjust a haptic actuator so that a contact pressure of the haptic actuator equals the second target contact pressure. Furthermore, when a plurality of haptic actuators are included in the wearable device 2000, the wearable device 2000 may calculate a second target contact pressure for each of the plurality of haptic actuators. The wearable device 2000 may select, from among the plurality of haptic actuators, haptic actuators determined to have a current contact pressure requiring adjustment. The wearable device may adjust only the selected haptic actuators so that contact pressures of the selected haptic actuators equal the second target contact pressure.

Moreover, although the method of FIG. 7 has been described with respect to an example in which the wearable device 2000 identifies the user's activity state by using acceleration sensor data, embodiments of the disclosure are not limited thereto. The wearable device 2000 may obtain a plurality of types of sensor data from a plurality of types of sensors included in a sensor unit, and identify whether the user's activity state is changed based on at least some of the obtained plurality of types of sensor data. For example, the wearable device 2000 may further use various types of sensors capable of measuring a user's movement, such as angular velocity data obtained from a gyro sensor. Methods, performed by the wearable device 2000, of calculating a difference based on obtained sensor data and updating a target contact pressure value may be equally applied to various types of sensor data.

Figure 8:
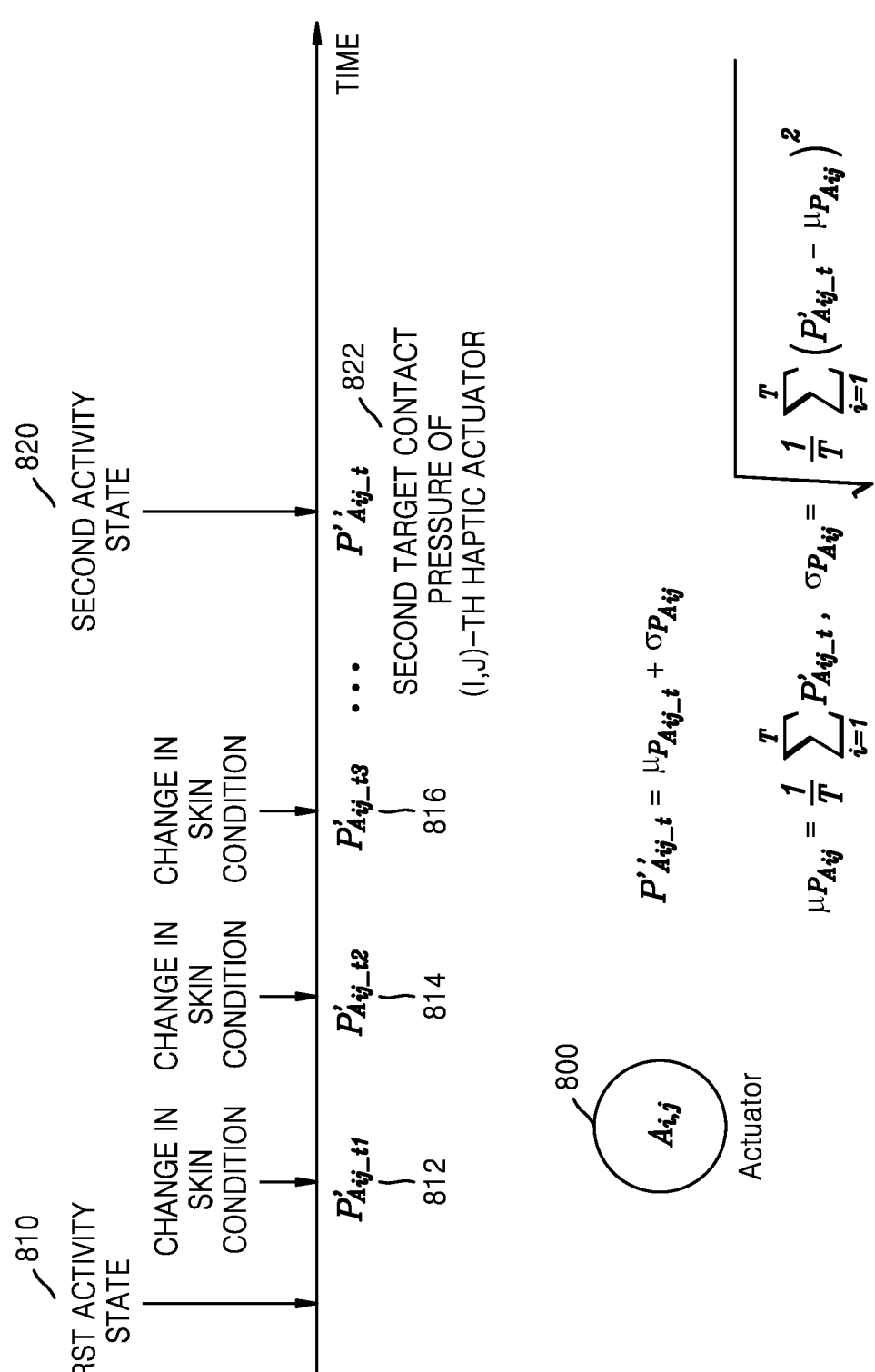
FIG. 8 is a diagram for describing a method, performed by a wearable device, of identifying a change in a user's activity state and determining a second target contact pressure, according to an embodiment of the disclosure.

FIG. 8 is a diagram for describing a method, performed by a wearable device, of identifying a change in a user's activity state and determining a second target contact pressure, according to an embodiment of the disclosure.

For convenience of description, the method of FIG. 8 will be described with respect to an example in which the wearable device 2000 calculate a second target contact pressure for an (i, j)-th haptic actuator $A_{i,j}$.

Referring to FIG. 8, according to an embodiment of the disclosure, the wearable device 2000 may identify whether a user's activity state is changed based on at least some of a plurality of types of sensor data obtained from a sensor unit. When it is identified that the user's activity state is changed, the wearable device 2000 may calculate a second target contact pressure. In this case, the second target contact pressure may be calculated based on a degree of change in a target contact pressure that has occurred before the user's activity state is changed.

In an embodiment of the disclosure, an activity state of the user of the wearable device 2000 may be a first activity state 810. For example, the first activity state 810 may be a 'normal' state in which the user is not exercising. When the user's activity state is the first activity state 810, the wearable device 2000 may identify whether a user's skin condition has changed, and determine a first target contact pressure as it is identified that the user's skin condition has changed. Because the method, performed by the wearable device 2000, of determining a first target contact pressure has been described above with reference to FIG. 6, a detailed description thereof will be omitted.

For example, when the user's activity state is the first activity state 810, the user's skin condition may change at time $t_1$. When it is identified that the user's skin condition has changed at time $t_1$, the wearable device 2000 may determine a first target contact pressure $P'_{A_{ij\_t1}}$ 812 at time $t_1$ based on user profile data and biometric data obtained at time $t_1$.

Furthermore, when the user's activity state is the first activity state 810, the user's skin condition may change again at time $t_2$. When it is identified that the user's skin condition has changed at time $t_2$, the wearable device 2000 may determine a first target contact pressure $P'_{A_{ij\_t2}}$ 814 at time $t_2$ based on the user profile data and biometric data obtained at time $t_2$.

In addition, when the user's activity state is the first activity state 810, the user's skin condition may change again at time $t_3$. When it is identified that the user's skin condition has changed at time $t_3$, the wearable device 2000 may determine a first target contact pressure $P'_{A_{ij\_t3}}$ 816 at time $t_3$ based on the user profile data and biometric data obtained at time $t_3$.

In the same way, each time the user's skin condition changes, the wearable device 2000 may determine a first target contact pressure based on the user profile data and biometric data at a time when the user's skin condition has changed.

In an embodiment of the disclosure, the wearable device 2000 may identify that the user's activity state is changed. The wearable device 2000 may identify that the user's activity state is changed from the first activity state 810 to a second activity state 820 at time t. In this case, the first activity state 810 may be a 'normal' state, and the second activity state 820 may be a 'running' state. Because the method, performed by the wearable device 2000, of analyzing a user's activity state has been described above with reference to FIG. 7, a detailed description thereof will be omitted.

The wearable device 2000 may calculate the second target contact pressure $P''_{A_{ij\_t}}$ 822 at time t as it is identified that the user's activity state is changed at time t. In this case, the second target contact pressure $P''_{A_{ij\_t}}$ 822 may be calculated using Equation 3 below.

$$P''_{A_{ij\_t}} = \mu_{P_{A_{ij}}} + \sigma_{P_{A_{ij}}} \qquad \text{Equation 3}$$

$$\mu_{P_{A_{ij}}} = \frac{1}{T}\sum\nolimits_{k=1}^{T} P'_{A_{ij\_t}},$$

$$\sigma_{P_{A_{ij}}} = \sqrt{\frac{1}{T}\sum\nolimits_{k=1}^{T}\left(P'_{A_{ij\_t}} - \mu_{P_{A_{ij}}}\right)^2}$$

where $P'_{A_{ij\_t}}$ and T respectively denote a first target contact pressure and a time duration of a previous activity state before the user's activity state is changed, and $\mu_{P_{A_{ij}}}$ and $\sigma_{P_{A_{ij}}}$ respectively denote a mean and a standard deviation of the first target contact pressures $P'_{A_{ij\_t}}$ changed over the time duration T.

In an embodiment of the disclosure, when a plurality of haptic actuators 800 are included in the wearable device 2000, the wearable device 2000 may determine a second target contact pressure $P''_{A_{ij}}$ for each of the plurality of haptic actuators, based on a degree of change in first target contact pressure for each of the plurality of haptic actuators.

Figure 9:
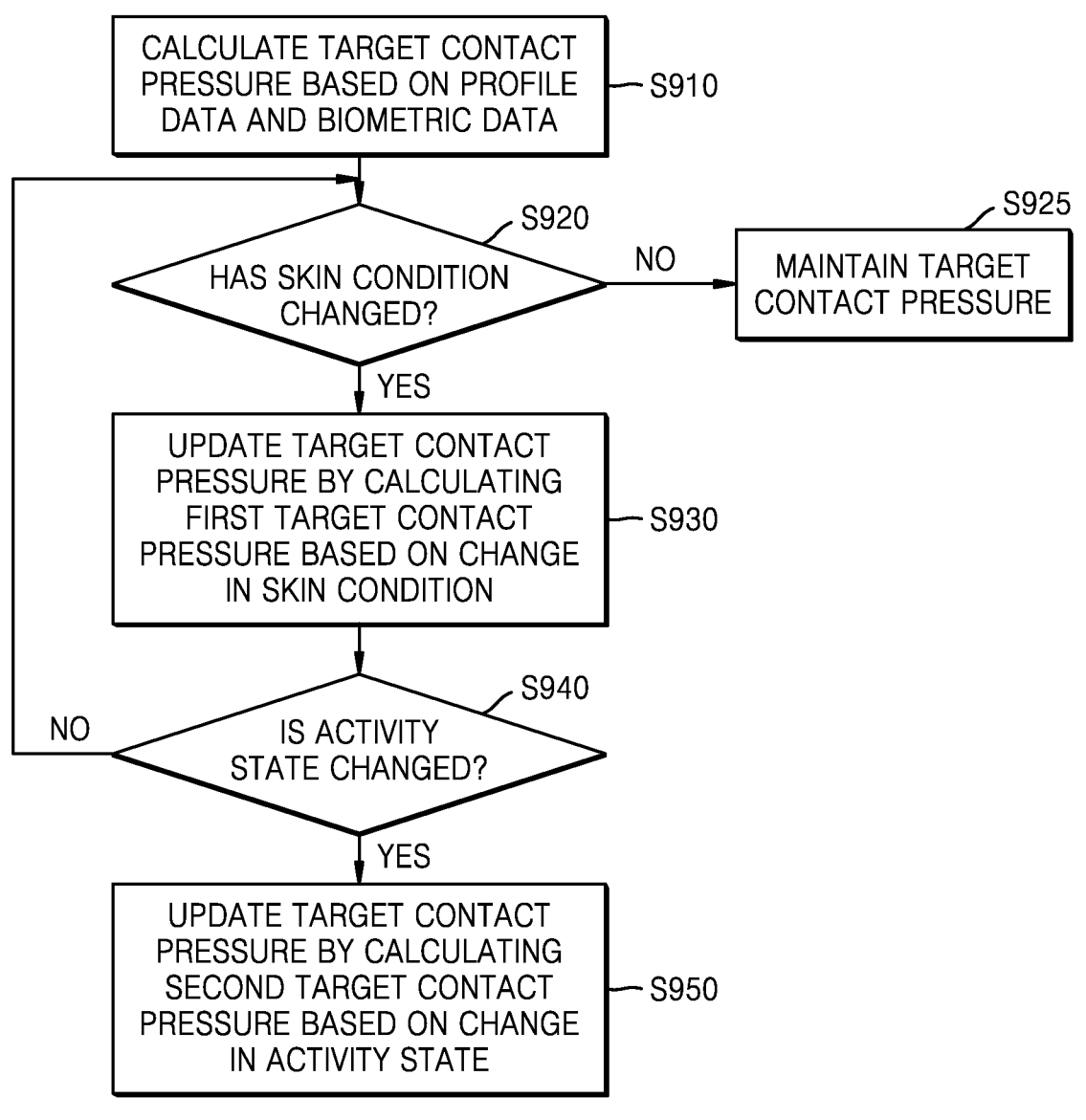
FIG. 9 is a flowchart of a method, performed by a wearable device, of updating a target contact pressure, according to an embodiment of the disclosure.

FIG. 9 is a flowchart of a method, performed by a wearable device, of updating a target contact pressure, according to an embodiment of the disclosure.

Referring to FIG. 9, in operation S910, the wearable device 2000 may calculate a target contact pressure for a haptic actuator based on user profile data and biometric data. Operation S910 of FIG. 9 may correspond to operation S330 of FIG. 3 or operation S460 of FIG. 4.

In operation S920, the wearable device 2000 may identify whether a user's skin condition has changed. When it is identified that the user's skin condition has not changed, the wearable device 2000 may maintain a target contact pressure (operation S925). When it is identified that the user's skin condition has changed, the wearable device 2000 may perform operation S930.

In operation S930, the wearable device 2000 may update a target contact pressure value by determining a first target contact pressure value based on the user's skin condition that has changed. Because the method of determining a first target contact pressure has been described with reference to FIG. 6, a detailed description thereof will be omitted.

In operation S940, the wearable device 2000 may identify whether the user's activity state is changed. When it is identified that the user's activity state is not changed, the wearable device 2000 may perform operation S920 again to monitor a change in the user's skin condition. When it is identified that the user's activity state is changed, the wearable device 2000 may perform operation S950.

In operation S950, the wearable device 2000 may update the target contact pressure value by determining a second target contact pressure value based on the changed user's activity state. Because the method of determining a second target contact pressure has been described above with reference to FIG. 8, a detailed description thereof will be omitted.

According to an embodiment of the disclosure, the wearable device 2000 may continuously update the target contact pressure value for the haptic actuator based on whether the user's skin condition has changed or whether the user's activity state is changed. The wearable device 2000 may measure a current contact pressure of the haptic actuator and adjust the haptic actuator so that the current contact pressure of the haptic actuator equals a target contact pressure.

Figure 10:
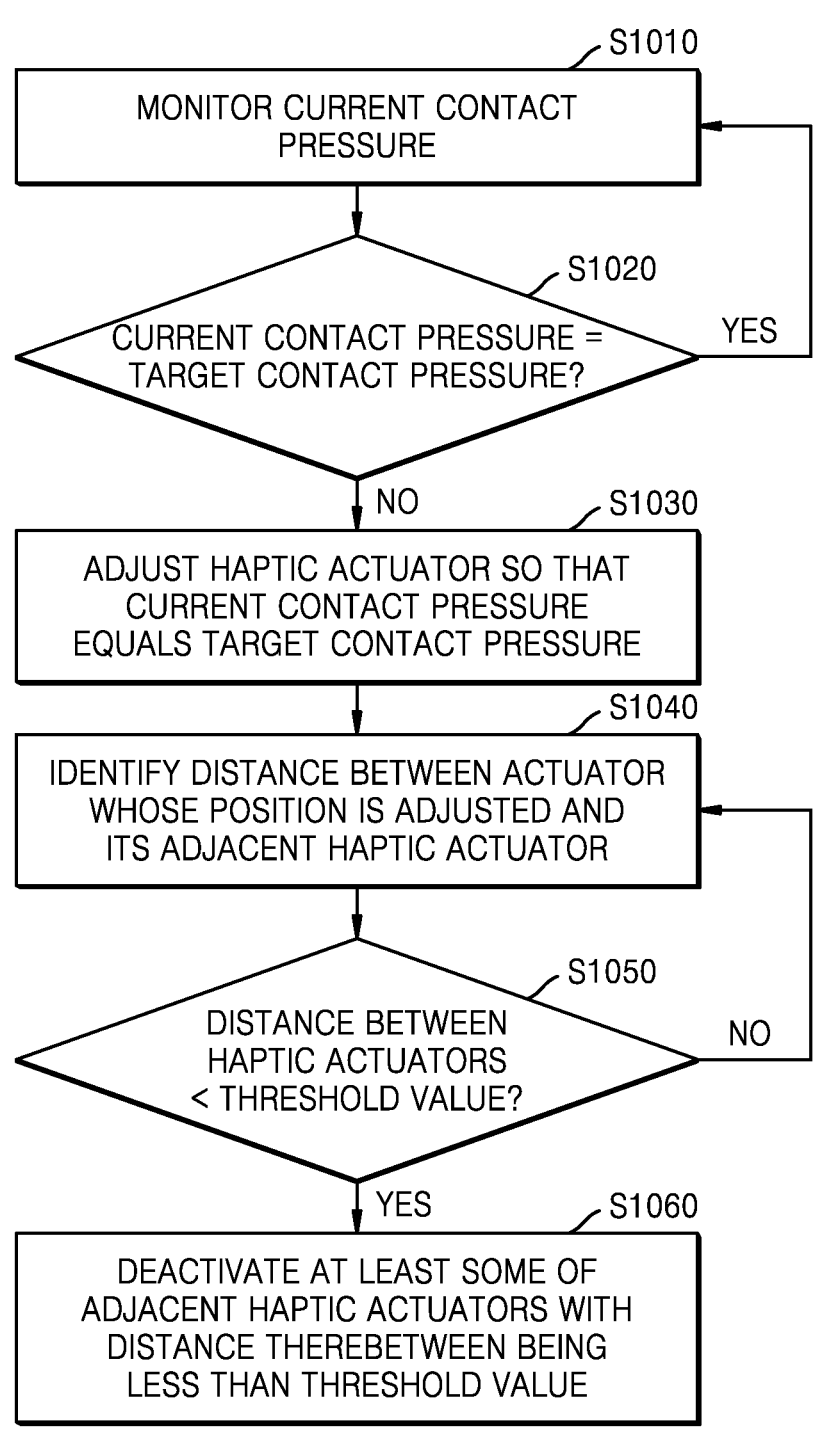
FIG. 10 is a flowchart of a method, performed by a wearable device, of adjusting a current contact pressure of a haptic actuator, according to an embodiment of the disclosure.

FIG. 10 is a flowchart of a method, performed by a wearable device, of adjusting a current contact pressure of a haptic actuator according to an embodiment of the disclosure.

Referring to FIG. 10, in operation S1010, the wearable device 2000 may monitor a current contact pressure of a haptic actuator. The wearable device 2000 may monitor the current contact pressure of the haptic actuator by obtaining data regarding a contact pressure applied to a user's body by the haptic actuator by using a pressure sensor included in the wearable device 2000 itself.

In operation S1020, the wearable device 2000 may compare the current contact pressure of the haptic actuator with a target contact pressure thereof. Because the method, performed by the wearable device 2000, of determining a target contact pressure value has been described in the above-described embodiments, a detailed description thereof will be omitted.

In an embodiment of the disclosure, when the current contact pressure of the haptic actuator is equal to the target contact pressure thereof, the wearable device 2000 may determine that the haptic actuator does not need to be adjusted. In this case, the wearable device 2000 may perform operation S1010 again to monitor the current contact pressure of the haptic actuator.

In an embodiment of the disclosure, the wearable device 2000 may perform operation S1030 when the current contact pressure of the haptic actuator is less or greater than the target contact pressure thereof.

In operation S1030, the wearable device 2000 may adjust the haptic actuator so that the contact pressure of the haptic actuator equals the target contact pressure thereof.

In an embodiment of the disclosure, when the current contact pressure of the haptic actuator is less than the target contact pressure thereof, the wearable device 2000 may adjust a position of the haptic actuator to be closer to the user's body, so that the haptic actuator may provide haptic feedback to the user while being in contact with the user's body at the target contact pressure.

In an embodiment of the disclosure, when the current contact pressure of the haptic actuator is greater than the target contact pressure thereof, the wearable device 2000 may adjust the position of the haptic actuator to be farther away from the user's body, so that the haptic actuator may provide haptic feedback to the user while being in contact with the user's body at the target contact pressure.

In operation S1040, the wearable device 2000 may identify a distance between the haptic actuator whose position is adjusted and each of its adjacent haptic actuators. For example, as the position of the haptic actuator is adjusted so that the current contact pressure thereof equals the target contact pressure in operation S1030, a distance between the haptic actuator whose position is adjusted and another haptic actuator included in the wearable device 2000 may increase or decrease. The wearable device 2000 may identify a distance between the haptic actuator whose position is adjusted and another haptic actuator.

In operation S1050, the wearable device 2000 may compare the identified distance between the haptic actuators with a threshold value. In an embodiment of the disclosure, when the identified distance between the haptic actuators is less than the threshold value, the wearable device 2000 may perform operation S1060.

In operation S1060, the wearable device 2000 may deactivate at least some of the adjacent haptic actuators with the distance therebetween less than the threshold value.

For example, when haptic feedback is generated from all of two or more adjacent haptic actuators with a distance therebetween of less than the threshold value, the haptic feedback may not be properly provided to the user due to the short distance between the haptic actuators (e.g., as in a case where the user feels haptic feedback generated from two or more adjacent haptic actuators as one piece of haptic feedback, etc.) Thus, because sufficient haptic feedback may be provided to the user even when haptic feedback is not generated from all of the two or more adjacent haptic actuators with the distance therebetween of less than the threshold value, the wearable device 2000 may deactivate at least some of the two or more adjacent haptic actuators with the distance of less than the threshold value.

Figure 11:
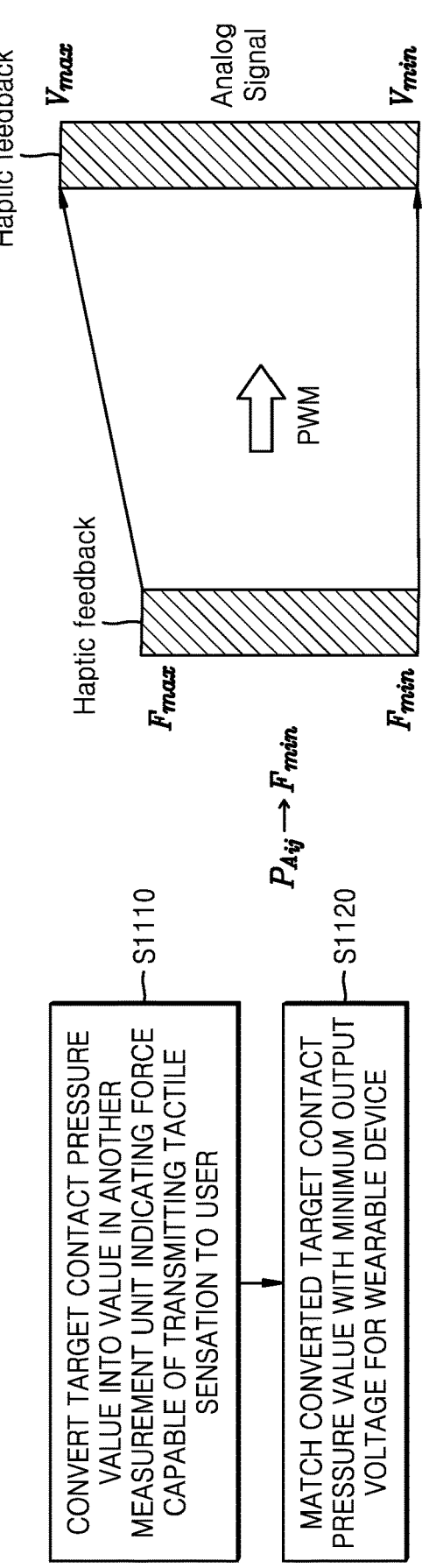
FIG. 11 is a diagram for describing a method, performed by a wearable device, of providing haptic feedback based on a target contact pressure, according to an embodiment of the disclosure.

FIG. 11 is a diagram for describing a method, performed by a wearable device, of providing haptic feedback based on a target contact pressure, according to an embodiment of the disclosure.

Referring to FIG. 11, in operation S1110, the wearable device 2000 may convert a target contact pressure value into a value expressed in another measurement unit indicating a force capable of transmitting a tactile sensation to a user. For example, the wearable device 2000 may convert the target contact pressure value $P_{A_{ij}}$ into a frequency value $F_{min}$ in Hz. The wearable device 2000 may set a frequency corresponding to the target contact pressure value to a minimum frequency $F_{min}$ of haptic feedback. However, the value in the other measurement unit is not limited thereto, and the wearable device 2000 may convert the target contact pressure value into a value expressed in another measurement unit such as ampere (A) indicating an energy capable of delivering haptic feedback to the user.

In operation S1120, the wearable device 2000 may match the value obtained by converting the target contact pressure value in operation S1110 with a minimum output voltage for the wearable device 2000. For example, the wearable device 2000 may match a frequency value $F_{min}$ in Hz obtained by converting the target contact pressure value $P_{A_{ij}}$ with a minimum output voltage $V_{min}$ for the wearable device 2000, such that a minimum intensity of the haptic feedback provided by the wearable device 2000 equals an intensity corresponding to the target contact pressure value.

The wearable device 2000 may adjust the intensity of the haptic feedback delivered to the user by using a PWM technique.

Figure 12:
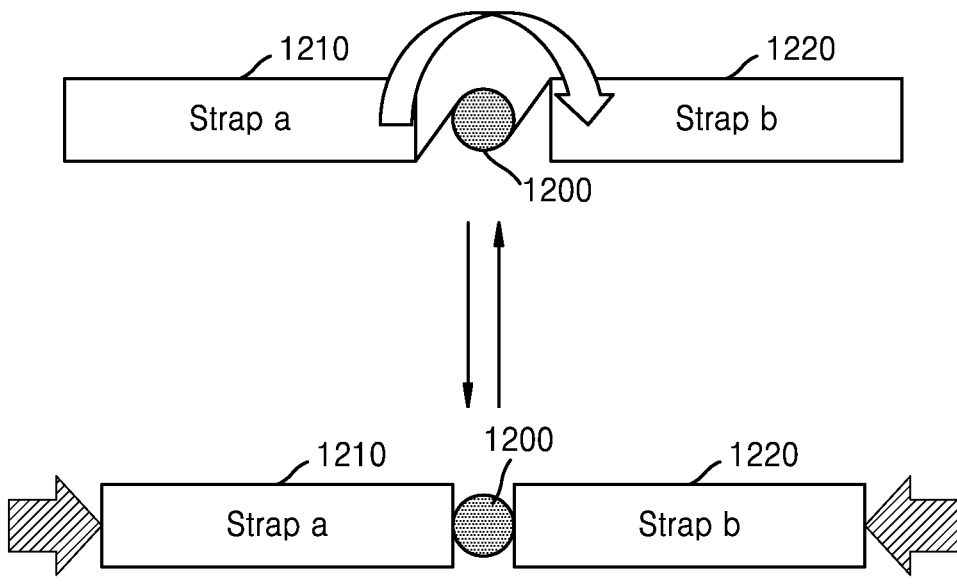
FIG. 12 is a diagram for describing an example in which a wearable device adjusts a haptic actuator to be in contact with a user's body, according to an embodiment of the disclosure.

FIG. 12 is a diagram for describing an example in which a wearable device adjusts a haptic actuator to be in contact with a user's body, according to an embodiment of the disclosure.

Referring to FIG. 12, in an embodiment of the disclosure, the wearable device 2000 may include a haptic actuator 1200 with a strap a 1210 connected to one side and a strap b 1220 connected to the other side thereof.

The wearable device 2000 may measure a current contact pressure of the haptic actuator 1200 and compare it with a target contact pressure thereof.

For example, when the current contact pressure is less than the target contact pressure, the wearable device 2000 may shorten the straps a and b in order to adjust a position of the haptic actuator 1200 to be closer to a user's body. For example, the wearable device 2000 may use a physical adjustment device (e.g., a gear, a string, etc.) attached to the haptic actuator 1200. The wearable device 2000 may adjust the position of the haptic actuator 1200 to be closer to the user's body by narrowing a distance between the haptic actuator 1200 and either of the straps a and b by tightening the strap a or b via the physical adjustment device so that the straps a and b are closer to the haptic actuator 1200.

In addition, when the current contact pressure is greater than the target contact pressure, the wearable device 2000 may adjust the position of the haptic actuator 1200 to be farther away from the user's body by widening a distance between the haptic actuator 1200 and either of the straps a and b by loosening the strap a or b. Physical structures used for the wearable device 2000 to adjust a position of a haptic actuator will be further described with reference to FIGS. 14A, 14B, and 15.

Figure 13:
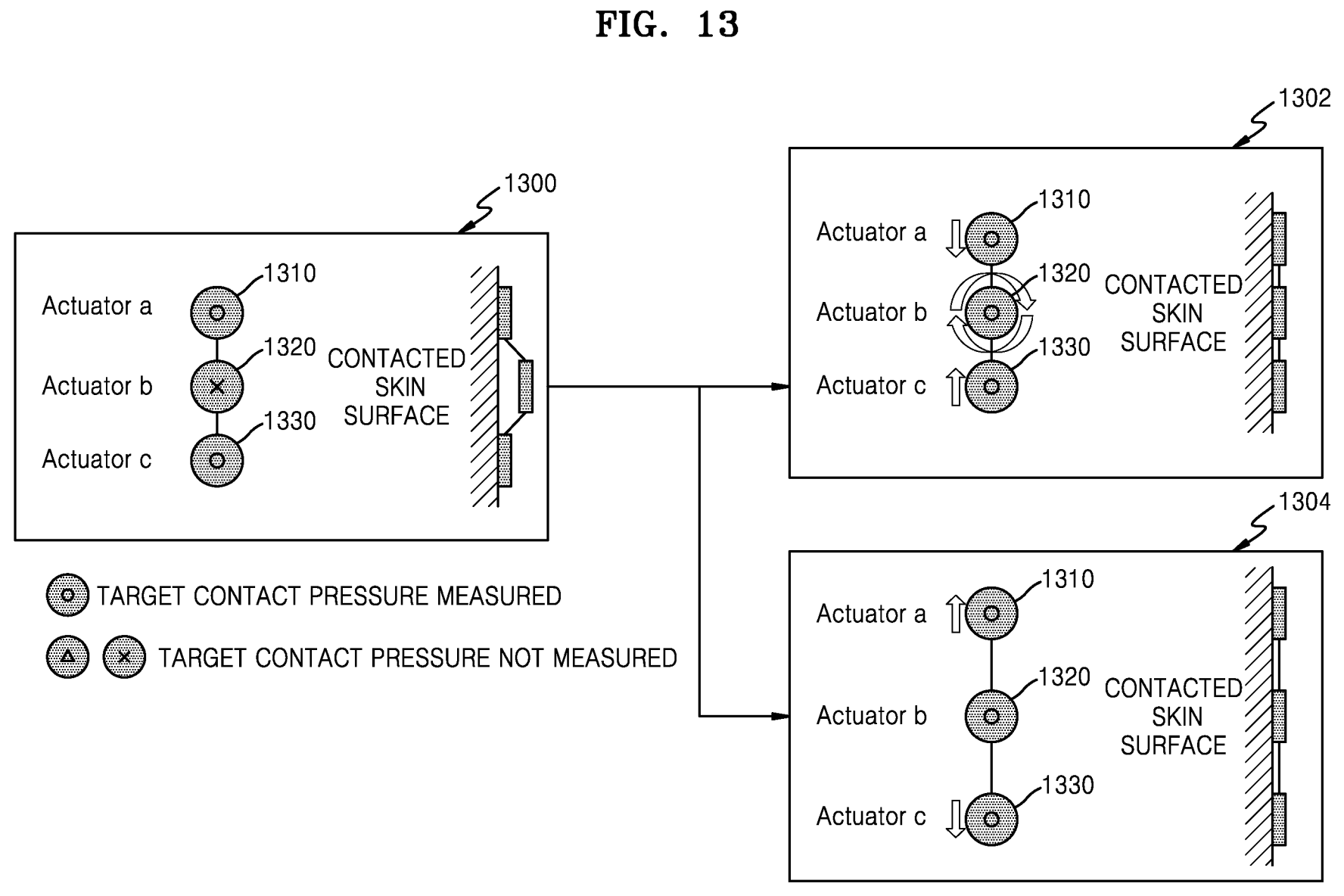

FIG. 13 is a diagram for describing a method, performed by a wearable device, of adjusting a distance between a plurality of haptic actuators in order to adjust a current contact pressure of the plurality of haptic actuators, according to an embodiment of the disclosure.

Referring to FIG. 13, in an embodiment of the disclosure, the wearable device 2000 may include a haptic actuator a 1310, a haptic actuator b 1320, and a haptic actuator c 1330.

Referring to block 1300, the haptic actuator a 1310 and the haptic actuator c 1330 may be positioned in contact with a user's skin. In this case, when current contact pressures of the haptic actuator a 1310 and the haptic actuator c 1330 are measured, it can be seen that the haptic actuator a 1310 and the haptic actuator c 1330 are appropriately in contact with the user's skin so that the measured current contact pressures equal corresponding target contact pressures.

However, the haptic actuator b 1320 may not be in contact with the user's skin. In this case, when a current contact pressure of the haptic actuator b 1320 is measured, the measured current contact pressure of the haptic actuator b 1320 may be less than a corresponding target contact pressure.

The wearable device 2000 may adjust a current contact pressure of a haptic actuator based on the current contact pressure and a target contact pressure of the haptic actuator. In this case, the wearable device 2000 may adjust the current contact pressure of the haptic actuator by adjusting distances between a plurality of haptic actuators.

For example, referring to block 1302, the wearable device 2000 may adjust the current contact pressure of the haptic actuator b 1320 by decreasing a distance between the haptic actuator a 1310 and the haptic actuator b 1320 and a distance between the haptic actuator b 1320 and the haptic actuator c 1330. The wearable device 2000 may tighten the haptic actuator b 1320 so that the haptic actuator a 1310 and the haptic actuator c 1330 are closer to the haptic actuator b 1320 to thereby bring the haptic actuator b 1320 into contact with the user's skin. In this case, the wearable device 2000 may adjust the current contact pressure of the haptic actuator b 1320 until the contact pressure of the haptic actuator b 1320 equals the target contact pressure.

As another example, referring to block 1304, the wearable device 2000 may adjust the current contact pressure of the haptic actuator b 1320 by increasing the distance between the haptic actuator a 1310 and the haptic actuator b 1320 and the distance between the haptic actuator b 1320 and the haptic actuator c 1330. The wearable device 2000 may pull the haptic actuator a 1310 and the haptic actuator c 1330 in a direction away from the haptic actuator b 1320 so that the haptic actuator a 1310 and the haptic actuator c 1330 are further away from the haptic actuator b 1320 to thereby bring the haptic actuator b 1320 into contact with the user's skin. In this case, the wearable device 2000 may adjust the current contact pressure of the haptic actuator b 1320 until the contact pressure of the haptic actuator b 1320 equals the target contact pressure.

Physical structures used for the wearable device 2000 to adjust a position of a haptic actuator will be further described with reference to FIGS. 14A, 14B, and 15.

Figure 14A:
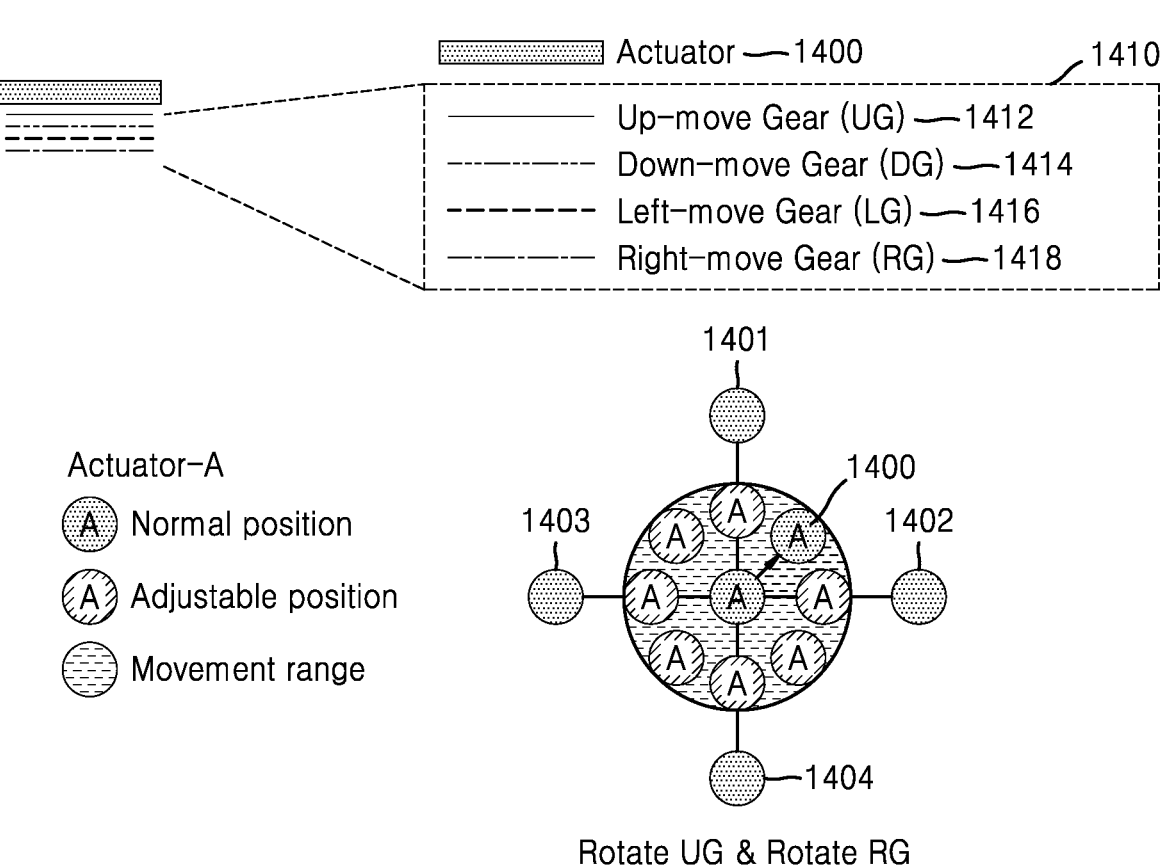
FIG. 14A is a diagram for describing a structure for adjusting, by a wearable device, a distance between a haptic actuator and each of its adjacent haptic actuators, according to an embodiment of the disclosure.

FIG. 14A is a diagram for describing a structure for adjusting, by a wearable device, a distance between a haptic actuator and each of its adjacent haptic actuators, according to an embodiment of the disclosure.

Referring to FIG. 14A, in an embodiment of the disclosure, the wearable device 2000 may include a gearbox 1410 connected to a haptic actuator 1400. The gearbox 1410 may include one or more gears. For example, the gearbox 1410 may include an up-move gear 1412, a down-move gear 1414, a left-move gear 1416, and a right-move gear 1418. However, embodiments of the disclosure are not limited thereto, and the gearbox 1410 may further include a front-move gear (not shown) and a back-move gear (not shown).

The wearable device 2000 may move the haptic actuator 1400 connected to the gearbox 1410 by rotating each of the gears included in the gearbox 1410.

For example, the wearable device 2000 may adjust a position of the haptic actuator 1400 so that the haptic actuator 1400 moves upward to the right by rotating the up-move gear 1412 and the right-move gear 1418. In this case, a distance between the haptic actuator 1400 and either haptic actuator 1401 or 1402 among the other haptic actuators 1401 through 1404 may decrease, while a distance between the haptic actuator 1400 and either of the haptic actuators 1403 and 1404 may increase.

According to an embodiment of the disclosure, the wearable device 2000 may perform distance adjustment to decrease or increase a distance between haptic actuators so that a haptic actuator contacts the user's body at a target contact pressure value.

FIG. 14B is a diagram for further describing the structure of FIG. 14A according to an embodiment of the disclosure.

According to an embodiment of the disclosure, the wearable device 2000 may adjust a distance between haptic actuators to which a gearbox is connected by controlling one or more gears among gears included in the gearbox to rotate. The wearable device 2000 may adjust a distance between the haptic actuators so that the haptic actuators come in contact with a user's body. In this case, the wearable device 2000 may control a haptic actuator so that a current contact pressure of the haptic actuator equals a target contact pressure thereof.

Referring to FIG. 14B, the wearable device 2000 according to an embodiment of the disclosure may control one or more gears from among the gears included in the gearbox 1410 to rotate. The wearable device 2000 may narrow a distance between the haptic actuator 1400 and another haptic actuator 1401 located above the haptic actuator 1400 by rotating the up-move gear 1412.

As another example, the wearable device 2000 may narrow a distance between the haptic actuator 1400 and another haptic actuator 1402 located to the right of the haptic actuator 1400 by rotating the right-move gear 1418.

As another example, the wearable device 2000 may narrow a distance between the haptic actuator 1400 and another haptic actuator 1403 located to the left of the haptic actuator 1400 by rotating the left-move gear 1416.

As another example, the wearable device 2000 may narrow a distance between the haptic actuator 1400 and another haptic actuator 1404 located below the haptic actuator 1400 by rotating the down-move gear 1414.

According to an embodiment of the disclosure, the wearable device 2000 may adjust a current contact pressure of a haptic actuator until it equals a target contact pressure by adjusting a distance between the haptic actuator and each of its adjacent haptic actuators.

Figure 15:
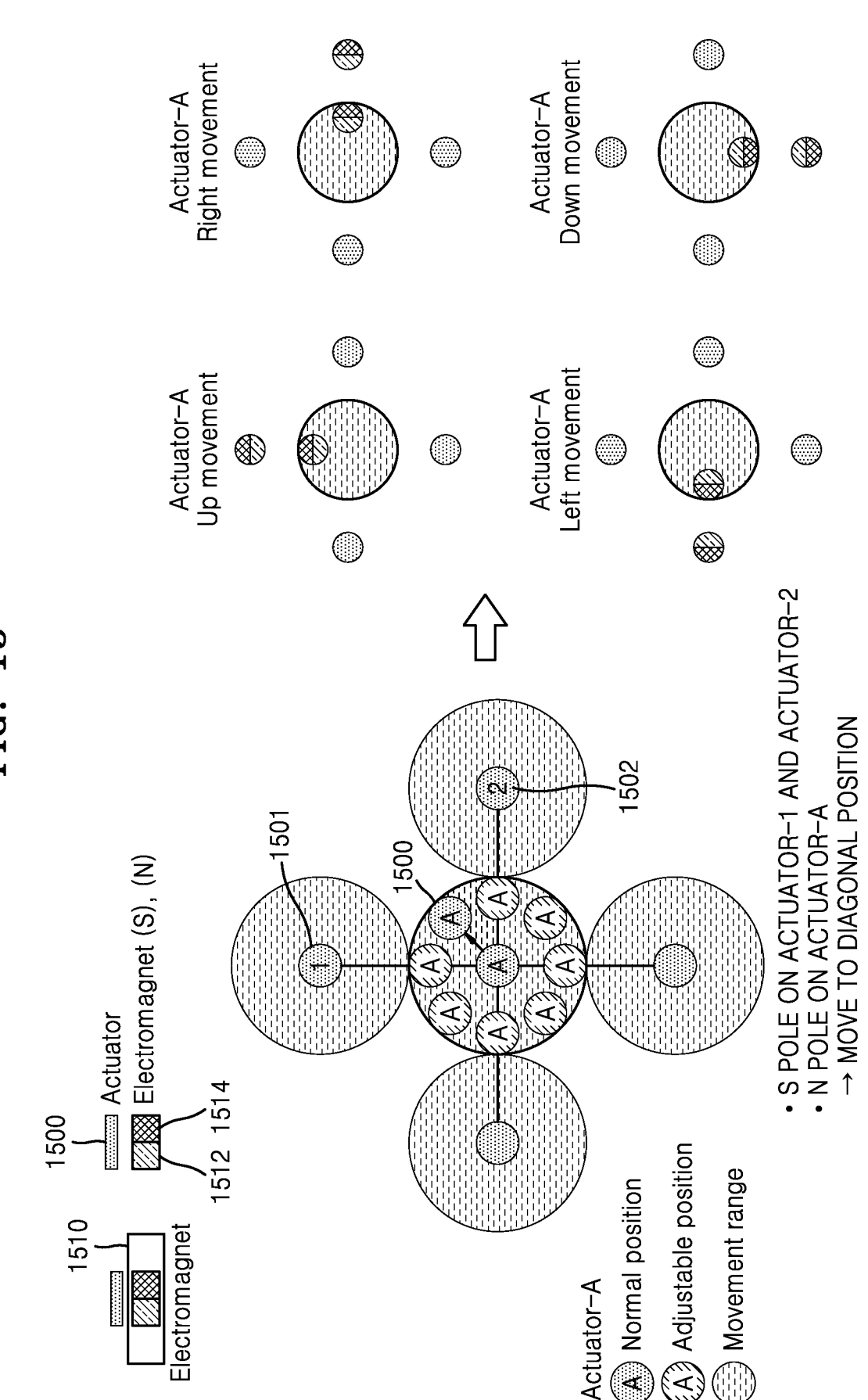
FIG. 15 is a diagram for describing another structure for adjusting, by a wearable device, a distance between a haptic actuator and each of its adjacent haptic actuators, according to an embodiment of the disclosure.

FIG. 15 is a diagram for describing another structure for adjusting, by a wearable device, a distance between a haptic actuator and each of its adjacent haptic actuators, according to an embodiment of the disclosure.

Referring to FIG. 15, in an embodiment of the disclosure, the wearable device 2000 may include an electromagnet 1510 attached to a haptic actuator 1500. The electromagnet 1510 may include a South (S) pole 1512 and a North (N) pole 1514. Positions of the S pole 1512 and the N pole 1514 may change depending on a direction of current flowing in the electromagnet 1510.

The wearable device 2000 may move the haptic actuator 1500 attached to the electromagnet 1510 by controlling the current flowing in the electromagnet 1510.

For example, by controlling the current flowing in the electromagnet 1510, the wearable device 2000 may adjust the haptic actuator 1500 attached to the electromagnet 1510 to move upward to the right. In this case, the current may flow such that other haptic actuators 1501 and 1502 are magnetized with an opposite pole to that of the haptic actuator 1500. Thus, a distance between the haptic actuator 1500 and either of the other haptic actuators 1501 and 1502 may be reduced.

According to an embodiment of the disclosure, the wearable device 2000 may perform distance adjustment to decrease or increase a distance between haptic actuators so that a haptic actuator contacts the user's body based on a target contact pressure value.

Figure 16:
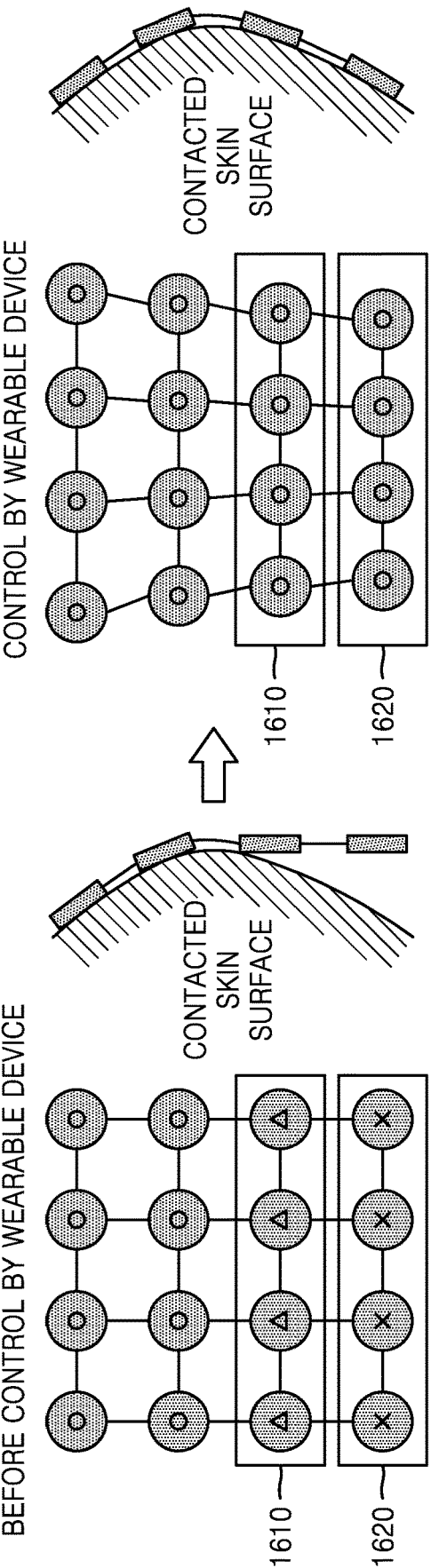
FIG. 16 is a diagram for describing a method, performed by a wearable device, of adjusting a distance between a plurality of haptic actuators in order to adjust a current contact pressure of the plurality of haptic actuators, according to an embodiment of the disclosure.

FIG. 16 is a diagram for describing a method, performed by a wearable device, of adjusting a distance between a plurality of haptic actuators in order to adjust a current contact pressure of the plurality of haptic actuators, according to an embodiment of the disclosure.

Referring to FIG. 16, in an embodiment of the disclosure, the wearable device 2000 may measure current contact pressures for a plurality of haptic actuators by using pressure sensors respectively corresponding to the plurality of haptic actuators.

The wearable device 2000 may select, based on the current contact pressures of the plurality of haptic actuators, one or more of the plurality of haptic actuators that have a current contact pressure to be adjusted.

For example, as a result of the wearable device 2000 measuring the current contact pressures of the plurality of haptic actuators, some of the haptic actuators may be haptic actuators 1610 that are incompletely in contact with a user's skin.

As another example, as a result of the wearable device 2000 measuring the current contact pressures of the plurality of haptic actuators, other haptic actuators may be haptic actuators 1620 that are not in contact with the user's skin.

The wearable device 2000 may select the haptic actuators 1610 and 1620 that are incompletely in contact with and not in contact with the user's skin from among the plurality of haptic actuators.

In an embodiment of the disclosure, the wearable device 2000 may adjust current contact pressures of the haptic actuators 1610 and 1620 that are incompletely in contact with and not in contact with the user's skin so as to equal their corresponding target contact pressures.

The wearable device 2000 may adjust the current contact pressures of the selected haptic actuators 1610 and 1620 that are incompletely in contact with and not in contact with the user's skin by adjusting a distance between the haptic actuators 1610 and 1620. In this case, the wearable device 2000 may adjust a distance between the haptic actuators 1610 and 1620 by using a gearbox or an electromagnet according to the embodiments of the disclosure.

Figure 17A:
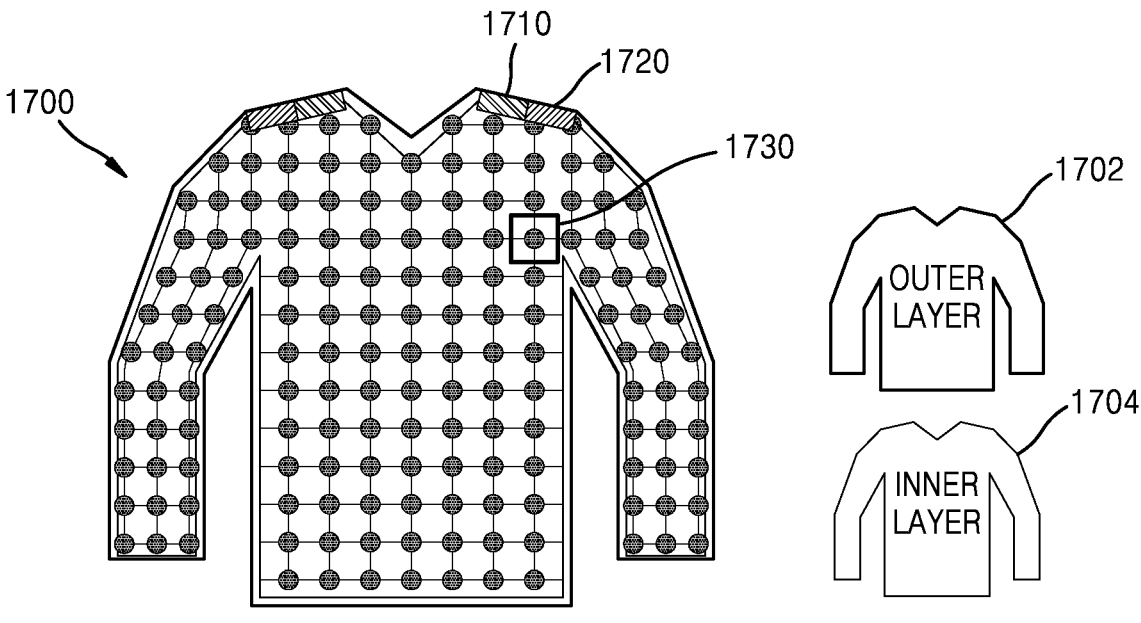
FIG. 17A is a diagram for describing a mounting structure for haptic actuators when a wearable device is smart clothing, according to an embodiment of the disclosure.

FIG. 17A is a diagram for describing a mounting structure for haptic actuators when a wearable device is smart clothing, according to an embodiment of the disclosure.

Referring to FIG. 17A, in an embodiment of the disclosure, the wearable device 2000 may be smart clothing 1700.

According to an embodiment of the disclosure, the smart clothing 1700 may include at least one battery 1710, at least one processor 1720, and a plurality of haptic actuators 1730. The battery 1710 may supply power required for the processor 1720 to control the smart clothing 1700. The processor 1720 may control each haptic actuator 1730 to generate haptic feedback. In addition, the processor 1720 may adjust a distance between the plurality of haptic actuators 1730 so that each of the plurality of haptic actuators 1730 contacts a user's body at a target contact pressure.

A sensor unit may be attached to each haptic actuator 1730 to obtain a plurality of types of sensor data. For example, the sensor unit may include a biosensor, a pressure sensor, an acceleration sensor, and a gyro sensor according to the embodiments of the disclosure.

In an embodiment of the disclosure, the smart clothing 1700 may be composed of an outer layer 1702 and an inner layer 1704. In this case, the plurality of haptic actuators 1730 may be mounted on the inner layer 1704 of the smart clothing 1700. The smart clothing 1700 may provide haptic feedback to the user wearing the smart clothing 1700 by using the plurality of haptic actuators 1730 arranged on the inner layer 1704 of the smart clothing 1700.

Figure 17B:
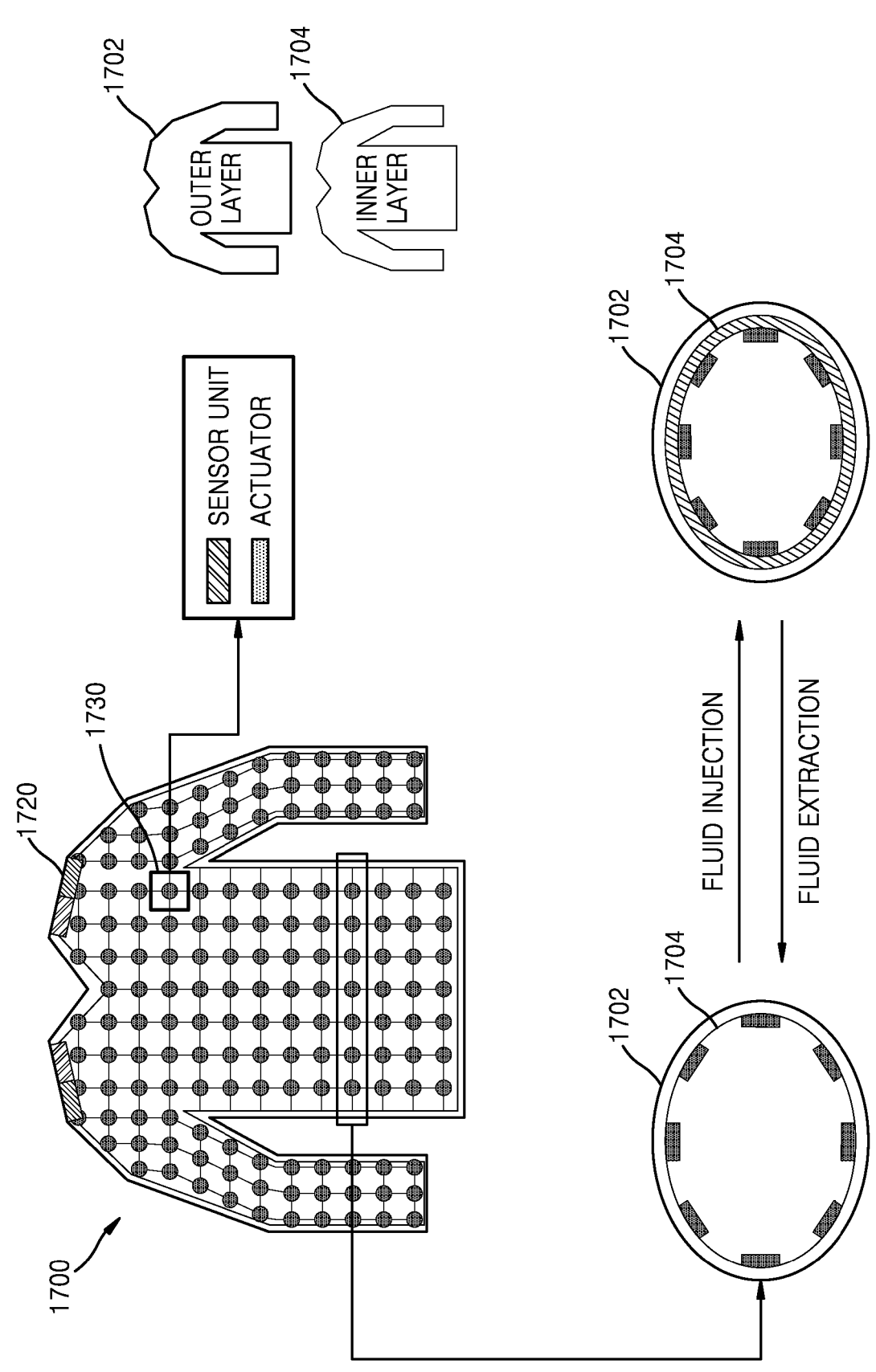
FIG. 17B is a diagram for describing a method of adjusting a current contact pressure of a haptic actuator by using a fluidic pressure when a wearable device is smart clothing, according to an embodiment of the disclosure.

FIG. 17B is a diagram for describing a method of adjusting a current contact pressure of a haptic actuator by using a fluidic pressure when a wearable device is smart clothing, according to an embodiment of the disclosure.

Referring to FIG. 17B, in an embodiment of the disclosure, a sensor unit may be attached to a haptic actuator 1730. The sensor unit may include a plurality of types of sensors and obtain a plurality of types of sensor data by using the plurality of types of sensors. For example, the sensor unit may include a biosensor, a pressure sensor, an acceleration sensor, and a gyro sensor.

In an embodiment of the disclosure, an inner layer 1704 of smart clothing 1700 may include a fluid pocket inflatable by a fluid. In this case, the smart clothing 1700 may further include a fluid pump for injecting a fluid into the fluid pocket.

A processor 1720 of the smart clothing 1700 may control the fluid pump so that the fluid is injected into or extracted from the fluid pocket. The processor 1720 may control the haptic actuator 1730 to come in contact with a user's body by injecting a fluid into the fluid pocket to inflate the fluid pocket.

When the haptic actuator 1730 comes in contact with the user's body, the processor 1720 may obtain a plurality of types of sensor data by using a plurality of types of sensors included in the sensor unit. The processor 1720 may calculate, based on the plurality of types of sensor data, a target contact pressure according to the embodiments of the disclosure. When the target contact pressure is calculated and updated, the processor 1720 may adjust a current contact pressure of the haptic actuator 1730 to equal the updated target contact pressure. In this case, the processor 1720 may adjust the current contact pressure of the haptic actuator 1730 by injecting a fluid into or extracting the fluid from the fluid pocket.

FIG. 17C is a diagram for describing a method of adjusting a current contact pressure of a haptic actuator by adjusting a distance between haptic actuators when a wearable device is smart clothing, according to an embodiment of the disclosure.

Referring to FIG. 17C, in an embodiment of the disclosure, a gearbox may be connected to each of a plurality of haptic actuators 1730 included in the smart clothing 1700. Furthermore, a sensor unit may be in contact with the haptic actuator 1730. The sensor unit may include a plurality of types of sensors and obtain a plurality of types of sensor data. For example, the sensor unit may include a biosensor, a pressure sensor, an acceleration sensor, and a gyro sensor.

The processor 1720 may measure current contact pressures of the plurality of haptic actuators 1730 by using pressure sensors respectively corresponding to the plurality of haptic actuators 1730.

The processor 1720 may select, based on the current contact pressures of the plurality of haptic actuators 1730, one or more of the plurality of haptic actuators 1730 that have a current contact pressure to be adjusted.

The processor 1720 may adjust the current contact pressure of the one or more selected haptic actuators to equal a target contact pressure. Because the method of adjusting a current contact pressure of a plurality of haptic actuators has been described with reference to FIG. 16, a detailed description thereof will be omitted.

FIG. 18A is a diagram for describing a method of adjusting a current contact pressure of a haptic actuator by using a fluidic pressure when a wearable device is a smart watch, according to an embodiment of the disclosure.

Referring to FIG. 18A, in an embodiment of the disclosure, the wearable device 2000 may be a smart watch 1800.

According to an embodiment of the disclosure, the smart watch 1800 may at least include a strap 1810, a fluid pocket 1820, a strap adjuster 1830, a sensor unit 1840, and a plurality of haptic actuators 1850.

In an embodiment of the disclosure, the plurality of haptic actuators 1850 may be arranged on the strap 1810. In addition, the fluid pocket 1820 that is inflatable by a fluid may be attached to the strap 1810.

In an embodiment of the disclosure, the strap adjuster 1830 may include a cylinder 1832, a fluid pump 1834 and a piston 1836 for injecting a fluid into the fluid pocket 1820. The strap adjuster 1830 may inject a fluid into or extract the fluid from the fluid pocket 1820 by using the cylinder 1832, the fluid pump 1834, and the piston 1836.

In an embodiment of the disclosure, a sensor unit 1840 may be attached to each haptic actuator 1850. The sensor unit 1840 may include a plurality of types of sensors and obtain a plurality of types of sensor data by using the plurality of types of sensors. For example, the sensor unit 1840 may include a biosensor, a pressure sensor, an acceleration sensor, and a gyro sensor.

The smart watch 1800 may control a fluid to be injected into or extracted from the fluid pocket 1820 by using the strap adjuster 1830. The smart watch 1800 may control the haptic actuator 1850 to come in contact with a user's body by injecting a fluid into the fluid pocket 1820 to inflate the fluid pocket 1820.

When the haptic actuator 1850 comes in contact with the user's body, the smart watch 1800 may obtain a plurality of types of sensor data by using a plurality of types of sensors included in the sensor unit 1840. The smart watch 1800 may calculate, based on the plurality of types of sensor data, a target contact pressure according to the embodiments of the disclosure. When the target contact pressure is calculated and updated, the smart watch 1800 may adjust a current contact pressure of the haptic actuator 1850 to equal the updated target contact pressure. In this case, the smart watch 1800 may adjust the current contact pressure of the haptic actuator 1850 by injecting a fluid into or extracting the fluid from the fluid pocket 1820 using the strap adjuster 1830.

FIG. 18B is a diagram for describing another method of adjusting a current contact pressure of a haptic actuator by adjusting a length of a strap when a wearable device is a smart watch, according to an embodiment of the disclosure.

Referring to FIG. 18B, in an embodiment of the disclosure, the wearable device 2000 may be a smart watch 1800.

According to an embodiment of the disclosure, the smart watch 1800 may at least include a strap 1810, a strap adjuster 1860, a sensor unit 1840, and a plurality of haptic actuators 1850.

In an embodiment of the disclosure, the plurality of haptic actuators 1850 may be arranged on the strap 1810.

In an embodiment of the disclosure, the strap adjuster 1860 may include a spring 1862 for adjusting a length of the strap 1810 and a gearbox 1864 including one or more gears. The strap adjuster 1860 may adjust the length of the strap 1810 by pulling or loosening the spring 1862 via the gearbox 1864.

In an embodiment of the disclosure, the sensor unit 1840 may be attached to each haptic actuator 1850. The sensor unit 1840 may include a plurality of types of sensors and obtain a plurality of types of sensor data by using the plurality of types of sensors. For example, the sensor unit 1840 may include a biosensor, a pressure sensor, an acceleration sensor, and a gyro sensor.

The smart watch 1800 may adjust a length of the strap 1810 by using the strap adjuster 1860. By rotating one or more gears included in the gearbox 1864 so that the spring 1862 is pulled, the smart watch 1800 may shorten the strap 1810 to control the haptic actuator 1850 to come in contact with a user's body.

When the haptic actuator 1850 comes in contact with the user's body, the smart watch 1800 may obtain a plurality of types of sensor data by using a plurality of types of sensors included in the sensor unit 1840. The smart watch 1800 may calculate, based on the plurality of types of sensor data, a target contact pressure according to the embodiments of the disclosure. When the target contact pressure is calculated and updated, the smart watch 1800 may adjust a current contact pressure of the haptic actuator 1850 to equal the updated target contact pressure. In this case, the smart watch 1800 may adjust the current contact pressure of the haptic actuator 1850 by tightening or loosening the strap 1810 using the strap adjuster 1860.

FIG. 19 is a diagram for describing a method of adjusting a current contact pressure of a haptic actuator by applying pressure to the haptic actuator when a wearable device is a head-mounted display, according to an embodiment of the disclosure.

Referring to FIG. 19, in an embodiment of the disclosure, the wearable device 2000 may be a head-mounted display 1900.

According to an embodiment of the disclosure, the head-mounted display 1900 may at least include a pad 1910, a pressure element 1920, a support member 1930, a sensor unit 1940, and a plurality of haptic actuators 1950. According to an embodiment of the disclosure, the head-mounted display 1900 may adjust a current contact pressure of each haptic actuator 1950 included in the head-mounted display 1900 by applying pressure to the haptic actuator 1950.

In an embodiment of the disclosure, the pad 1910 may be in contact with a user's body. In addition, the plurality of haptic actuators 1950 may be arranged on a surface opposite to a contact surface where the pad 1910 is in contact with the user's body.

In an embodiment of the disclosure, the pressure element 1920 may apply pressure towards the haptic actuator 1950 included in the pad 1910 to bring the haptic actuator 1950 into close contact with the user's body.

The support member 1930 may support the pressure element 1920 for applying pressure to the haptic actuator 1950.

In an embodiment of the disclosure, the sensor unit 1940 may be attached to each haptic actuator 1950. The sensor unit 1940 may include a plurality of types of sensors and obtain a plurality of types of sensor data by using the plurality of types of sensors. For example, the sensor unit 1940 may include a biosensor, a pressure sensor, an acceleration sensor, and a gyro sensor.

The head-mounted display 1900 may control the haptic actuator 1950 to come in contact with the user's body by applying pressure to the haptic actuator 1950 using the pressure element 1920.

For example, referring to block 1902, the head-mounted display 1900 may apply pressure to the haptic actuator 1950 by using the pressure element 1920, so that the haptic actuator 1950 come in contact with a user's forehead. Furthermore, referring to block 1904, the head-mounted display 1900 may apply pressure to the haptic actuator 1950 by using the pressure element 1920, so that haptic actuator 1950 come in contact with the user's nose and cheekbones.

In an embodiment of the disclosure, the pressure element 1920 may include various structures capable of applying pressure to the haptic actuator 1950. For example, the pressure element 1920 may be a hydraulic pressure element, a spring, a shape memory alloy spring, or the like, but is not limited thereto.

For convenience of description, when it is assumed that the pressure element 1920 is a shape memory alloy spring, the head-mounted display 1900 applies pressure to the haptic actuator 1950 by heating the shape memory alloy spring, so that the haptic actuator 1950 is controlled to come in contact with the user's body.

FIG. 20 is a block diagram of a configuration of a server according to an embodiment of the disclosure.

Referring to FIG. 20, a server 3000 according to an embodiment of the disclosure may interconnect with the wearable device 2000 by using a wired or wireless communication method, and perform data communication therewith.

According to an embodiment of the disclosure, the server 3000 may at least include a communication interface 3100, a DB 3200, a memory 3300, and a processor 3400.

According to an embodiment of the disclosure, the communication interface 3100 may include one or more components that enable communication via a local area network (LAN), a wide area network (WAN), a value added network (VAN), a mobile radio communication network, a satellite communication network, and combinations thereof.

According to an embodiment of the disclosure, the communication interface 3100 may transmit an AI model for determining a target contact pressure to the wearable device 2000. Furthermore, the communication interface 3100 may receive user profile data and biometric data from the wearable device 2000, and transmit, to the wearable device 2000, a target contact pressure calculated using the AI model for determining the target contact pressure, which is stored in the server 3000. In addition, the communication interface 3100 may receive the AI model for determining a target contact pressure from the wearable device 2000, and transmit an updated AI model to the wearable device 2000.

The DB 3200 may store data received from the wearable device 2000. The DB 3200 may store an AI model generated via training in the server 3000 and a training dataset to be used to train the AI model.

The memory 3300 may store various pieces of data, programs, or applications for driving and controlling the server 3000. A program stored in the memory 3300 may include one or more instructions. A program (one or more instructions) or an application stored in the memory 3300 may be executed by the processor 3400. A module performing the same function as a module stored in the wearable device 2000 may be stored in the memory 3300. For example, data and program instruction codes corresponding to a sensor data analysis module (not shown) and a target contact pressure determination module (not shown) may be stored in the memory 3300.

The processor 3400 may control all operations of the server 3000. According to an embodiment of the disclosure, the processor 3400 may execute one or more programs stored in the memory 3300.

According to an embodiment of the disclosure, the processor 3400 may include, but is not limited to, an AP, a CPU, a GPU, an NPU, or an AI processor designed with a hardware structure specialized for processing an AI model.

The processor 3400 may perform operations that may be performed by the wearable device 2000 according to the embodiments of the disclosure.

The processor 3400 may calculate a target contact pressure that is a pressure set so that a haptic actuator of the wearable device 2000 is in contact with a user's body. The processor 3400 may receive user profile data and biometric data from the wearable device 2000, and determine a target contact pressure for a haptic actuator included in the wearable device 2000 by using an AI model for determining a target contact pressure, which is stored in the DB 3200. Because a method, performed by the server 3000, of determining a target contact pressure corresponds to the method, performed by the wearable device 2000, of determining a target contact pressure, a detailed description thereof will be omitted.

The processor 3400 may generate an AI model for determining a target contact pressure by performing training based on user profile data and biometric data stored in the DB 3200. The generated AI model may be transmitted to the wearable device 2000.

The processor 3400 may receive, from the wearable device 2000, a plurality of pieces of sensor data obtained as the user actually uses the wearable device 2000 and update the AI model for determining a target contact pressure.

Moreover, the block diagrams of the wearable device 2000 of FIG. 2 and the server 3000 of FIG. 20 may be provided for illustration of embodiments of the disclosure. Each of the components in the block diagram may be integrated, added, or omitted according to the specification of each device that is actually implemented. In other words, two or more components may be combined into a single component, or a single component may be split into two or more components when necessary. Furthermore, functions performed in each block are intended to describe the embodiments of the disclosure, and a specific operation or apparatus related to the functions does not limit the scope of the disclosure.

An operation method of a wearable device according to an embodiment of the disclosure may be implemented in the form of program instructions executable by various types of computers and be recorded on computer-readable recording media. The computer-readable recording media may include program instructions, data files, data structures, etc. either alone or in combination. The program instructions recorded on the computer-readable recording media may be designed and configured specially for the disclosure or may be known to and be usable by those skilled in the art of computer software. Examples of the computer-readable recording media include magnetic media such as hard disks, floppy disks, and magnetic tape, optical media such as compact disk-ROM (CD-ROM) and digital versatile disks (DVDs), magneto-optical media such as floptical disks, and hardware devices that are specially configured to store and perform program instructions, such as ROM, RAM, flash memory, etc. Examples of program instructions include not only machine code such as that generated by a compiler but also high-level language code executable by a computer using an interpreter or the like.

Furthermore, operation methods of an electronic device according to embodiments of the disclosure may be included in a computer program product when provided. The computer program product may be traded, as a product, between a seller and a buyer.

The computer program product may include a software program and a computer-readable storage medium having stored thereon the software program. For example, the computer program product may include a product (e.g., a downloadable application) in the form of a software program electronically distributed by a manufacturer of a wearable device or through an electronic market. For such electronic distribution, at least a part of the software program may be stored on the storage medium or may be temporarily generated. In this case, the storage medium may be a storage medium of a server of the manufacturer, a server of the electronic market, or a relay server for temporarily storing the software program.

In a system consisting of a server and a client device, the computer program product may include a storage medium of the server or a storage medium of the client device. Alternatively, in a case where a third device (e.g., a smartphone) is communicatively connected to the server or client device, the computer program product may include a storage medium of the third device. Alternatively, the computer program product may include a software program itself that is transmitted from the server to the client device or the third device or that is transmitted from the third device to the client device.

In this case, one of the server, the client device, and the third device may execute the computer program product to perform methods according to embodiments of the disclosure. Alternatively, two or more of the server, the client device, and the third device may execute the computer program product to perform the methods according to the embodiments of the disclosure in a distributed manner.

For example, the server (e.g., a cloud server, an AI server, or the like) may execute the computer program product stored therein to control the client device communicatively connected to the server to perform the methods according to the embodiments of the disclosure.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. A wearable device for providing haptic feedback, the wearable device comprising:
    a sensor configured to obtain a plurality of types of sensor data, the sensor including:
        one or more biosensors configured to obtain biometric data of a user, and
        one or more pressure sensors configured to obtain data regarding a contact pressure applied to a body of the user by one or more haptic actuators;
    the one or more haptic actuators configured to provide haptic feedback to the user;
    memory, comprising one or more storage media, storing instructions; and
    one or more processors communicatively coupled to the sensor and the memory,
    wherein the instructions, when executed by the one or more processors individually or collectively, cause the wearable device to:
        obtain profile data of the user,
        obtain the biometric data of the user from the one or more biosensors,
        calculate, based on the profile data and the biometric data of the user, a target contact pressure to be applied to the body of the user by the one or more haptic actuators,
        measure a current contact pressure applied to the body of the user by the one or more haptic actuators by using the one or more pressure sensors,
        adjust the current contact pressure of the one or more haptic actuators based on the current contact pressure and the target contact pressure by controlling the one or more haptic actuators to be in contact with the user's body based on the current contact pressure and the target contact pressure, and
        provide, using the one or more haptic actuators having the adjusted contact pressure, haptic feedback to the user,
    wherein the wearable device includes physical structures capable of adjusting a position of the one or more haptic actuators to be closer to or farther away from the user's body.

2. The wearable device of claim 1,
    wherein the biometric data of the user includes sensor data for identifying at least one of a skin condition or an activity state of the user, and
    wherein the profile data of the user includes information about at least one of an age, a gender, body attributes, or a skin type of the user.

3. The wearable device of claim 2, wherein the instructions, when executed by the one or more processors individually or collectively, further cause the wearable device to execute the one or more instructions to determine the target contact pressure by applying the profile data of the user, and the identified at least one of the skin condition, or the activity state to an artificial intelligence model trained to determine the target contact pressure.

4. The wearable device of claim 1,
    wherein the one or more haptic actuators are a plurality of haptic actuators,
    wherein the one or more pressure sensors are a plurality of pressure sensors, and wherein the one or more biosensors are a plurality of biosensors that obtain the biometric data, and wherein the instructions, when executed by the one or more processors individually or collectively, further cause the wearable device to:

respectively calculate target contact pressures of the plurality of haptic actuators based on the profile data and the biometric data of the user, and respectively measure current contact pressures of the plurality of haptic actuators by using the plurality of pressure sensors.

5. The wearable device of claim 4, wherein the instructions, when executed by the one or more processors individually or collectively, further cause the wearable device to:

select, based on the current contact pressures of the plurality of haptic actuators, one or more haptic actuators that have a current contact pressure to be adjusted from among the plurality of haptic actuators, and adjust the current contact pressure of the selected one or more haptic actuators by controlling the selected one or more haptic actuators to be in contact with the user's body based on the current contact pressure and the target contact pressure.

6. The wearable device of claim 5, wherein the instructions, when executed by the one or more processors individually or collectively, further cause the wearable device to:

identify, based on the biometric data, whether a skin condition of the user has changed, when the skin condition of the user is identified as having changed, change the target contact pressures of the plurality of haptic actuators based on the profile data and the biometric data of the user, and readjust a current contact pressure of at least some of the plurality of haptic actuators by controlling the at least some of the plurality of haptic actuators to be in contact with the user's body based on the current contact pressure and the target contact pressure.

7. The wearable device of claim 6, wherein instructions, when executed by the one or more processors individually or collectively, further cause the wearable device to:

identify whether an activity state of the user has changed based on at least some of the plurality of types of sensor data obtained from the sensor, and when the activity state of the user is identified as having changed, change the target contact pressures of the plurality of haptic actuators to new target contact pressures based on a degree of change in the target contact pressures that occurred before the activity state of the user is changed.

8. The wearable device of claim 7, wherein the instructions, when executed by the one or more processors individually or collectively, further cause the wearable device to readjust a current contact pressure of at least some of the plurality of haptic actuators, based on the new target contact pressure and a current contact pressure sensed by each of the plurality of pressure sensors.

9. The wearable device of claim 5, wherein the instructions, when executed by the one or more processors individually or collectively, further cause the wearable device to adjust the current contact pressure of the selected one or more haptic actuators by adjusting a distance between the selected one or more haptic actuators and each haptic actuator adjacent to the selected one or more haptic actuators.

10. The wearable device of claim 5, wherein the instructions, when executed by the one or more processors individually or collectively, further cause the wearable device to adjust the current contact pressure of the selected one or more haptic actuators by applying pressure to the selected one or more haptic actuators.

11. A method, performed by a wearable device, of providing haptic feedback, the method comprising:

obtaining profile data of a user;

obtaining biometric data of the user by using one or more biosensors;

calculating, based on the profile data and the biometric data of the user, a target contact pressure to be applied to a body of the user by one or more haptic actuators;

measuring a current contact pressure applied to the body of the user by the one or more haptic actuators by using one or more pressure sensors;

adjusting the current contact pressure of the one or more haptic actuators based on the current contact pressure and the target contact pressure by adjusting, using physical structures of the wearable device, a position of the one or more haptic actuators to be closer to or farther away from the user's body so as to be in contact with the user's body; and providing, using the one or more haptic actuators having the adjusted contact pressure, haptic feedback to the user.

12. The method of claim 11, wherein the biometric data of the user includes sensor data for identifying at least one of a skin condition or an activity state of the user, and wherein the profile data of the user includes information about at least one of an age, a gender, body attributes, or a skin type of the user.

13. The method of claim 12, wherein the calculating of the target contact pressure comprises determining the target contact pressure by applying the profile data of the user, the identified at least one of the skin condition, and the activity state to an artificial intelligence model trained to determine the target contact pressure.

14. The method of claim 11, wherein the one or more haptic actuators are a plurality of haptic actuators, the one or more pressure sensors are a plurality of pressure sensors, and the one or more biosensors are a plurality of biosensors that obtain the biometric data, wherein the calculating of the target contact pressure comprises respectively calculating target contact pressures of the plurality of haptic actuators based on the profile data and the biometric data of the user, and wherein the measuring of the current contact pressure comprises respectively measuring current contact pressures of the plurality of haptic actuators by using the plurality of pressure sensors.

15. The method of claim 14, further comprising:

selecting, based on the current contact pressures of the plurality of haptic actuators, one or more haptic actuators that have a current contact pressure to be adjusted from among the plurality of haptic actuators, wherein the adjusting of the current contact pressure of the one or more haptic actuators comprises adjusting the current contact pressure of the selected one or more haptic actuators by controlling the selected one or more haptic actuators to be in contact with the user's body based on the current contact pressure and the target contact pressure.

16. The method of claim 15, further comprising:

identifying, based on the biometric data, whether a skin condition of the user has changed, wherein the calculating of the target contact pressure comprises, when the skin condition of the user is identified as having changed, changing the target contact pressures of the plurality of haptic actuators based on the profile data and the biometric data of the user, and wherein the adjusting of the current contact pressure of the one or more haptic actuators comprises readjusting a current contact pressure of at least some of the plurality of haptic actuators by controlling the at least some of the plurality haptic actuators to be in contact with the user's body based on the current contact pressure and the target contact pressure.

17. The method of claim 16, further comprising:

obtaining a plurality of types of sensor data from a sensor unit; and identifying whether an activity state of the user has changed based on at least some of the plurality of types of sensor data obtained from the sensor unit, wherein the calculating of the target contact pressure comprises, when the activity state of the user is identified as having changed, changing the target contact pressures of the plurality of haptic actuators to new target contact pressures based on a degree of change in the target contact pressures that occurred before the activity state of the user is changed.

18. The method of claim 17, wherein the adjusting of the current contact pressure comprises readjusting a current contact pressure of at least some of the plurality of haptic actuators, based on the new target contact pressure and a current contact pressure sensed by each of the plurality of pressure sensors.

19. The method of claim 15, wherein the adjusting of the current contact pressure comprises adjusting the current contact pressure of the selected one or more haptic actuators by adjusting a distance between the selected one or more haptic actuators and each haptic actuator adjacent to the selected one or more haptic actuators.

20. One or more non-transitory computer-readable recording media storing one or more computer programs including computer-executable instructions that, when executed by one or more processors of a wearable device individually or collectively, cause the wearable device to perform operations, the operations comprising:

obtaining profile data of a user;

obtaining biometric data of the user by using one or more biosensors;

calculating, based on the profile data and the biometric data of the user, a target contact pressure to be applied to a body of the user by one or more haptic actuators;

measuring a current contact pressure applied to the body of the user by the one or more haptic actuators by using one or more pressure sensors;

adjusting the current contact pressure of the one or more haptic actuators based on the current contact pressure and the target contact pressure by adjusting, using physical structures of the wearable device, a position of the one or more haptic actuators to be closer to or farther away from the user's body so as to be in contact with the user's body; and providing, using the one or more haptic actuators having the adjusted contact pressure, haptic feedback to the user.

* * * * *